United States Patent
Wheeler et al.

(10) Patent No.: US 7,169,963 B2
(45) Date of Patent: Jan. 30, 2007

(54) MAMMALS EXPRESSING IGF-1 AND ALPHA-LACTALBUMIN IN THEIR MILK

(75) Inventors: Matthew B. Wheeler, Tolono, IL (US); Sharon M. Donovan, Champaign, IL (US); Gregory T. Bleck, Baraboo, WI (US); Marcia Monaco-Siegel, Sidney, IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 332 days.

(21) Appl. No.: 10/676,566

(22) Filed: Sep. 30, 2003

(65) Prior Publication Data

US 2004/0064841 A1   Apr. 1, 2004

Related U.S. Application Data

(62) Division of application No. 09/930,377, filed on Aug. 15, 2001, now Pat. No. 6,677,500.

(60) Provisional application No. 60/225,474, filed on Aug. 15, 2000.

(51) Int. Cl.
*A01K 67/27* (2006.01)
*C12P 21/00* (2006.01)

(52) U.S. Cl. .............. 800/14; 800/7; 800/15; 800/16; 800/17; 800/18

(58) Field of Classification Search ........... 800/14–18, 800/4, 7; 426/580
See application file for complete search history.

(56) References Cited

U.S. PATENT DOCUMENTS

| | | | |
|---|---|---|---|
| 4,736,866 A | 4/1988 | Leder et al. | 800/1 |
| 4,873,191 A | 10/1989 | Wagner et al. | 435/172.3 |
| 4,873,316 A | 10/1989 | Meade et al. | 530/412 |
| 4,994,384 A | 2/1991 | Prather et al. | 435/172.2 |
| 5,057,420 A | 10/1991 | Massey | 435/172.2 |
| 5,304,489 A | 4/1994 | Rosen | 435/320.1 |
| 5,453,457 A | 9/1995 | Meltzer et al. | 523/136 |
| 5,496,720 A | 3/1996 | Susko-Parrish et al. | 435/240.2 |
| 5,523,226 A | 6/1996 | Wheeler | 435/240.2 |
| 5,530,177 A | 6/1996 | Bleck et al. | 800/2 |

(Continued)

FOREIGN PATENT DOCUMENTS

EP         117058         9/1989

(Continued)

OTHER PUBLICATIONS

Ristevski. Making Better Transgenic Models. Molecular Biotechnology. 2005, vol. 29, pp. 153-164.*

(Continued)

*Primary Examiner*—Deborah Crouch
(74) *Attorney, Agent, or Firm*—Greenlee, Winner and Sullivan, P.C.

(57) ABSTRACT

The present invention relates to animals that express exogenous growth factors in their milk, and in particular to pigs that express exogenous IGF-I in their milk. The present invention also relates to methods for increasing piglet weight gain and intestinal lactase activity. The present invention thus provides a method of facilitating piglet development and decreasing piglet mortality.

6 Claims, 13 Drawing Sheets

U.S. PATENT DOCUMENTS

| | | | |
|---|---|---|---|
| 5,534,493 A | 7/1996 | Gluckman et al. | |
| 5,565,362 A | 10/1996 | Rosen | 435/320.1 |
| 5,686,120 A | 11/1997 | Mertz et al. | 435/320.1 |
| 5,831,141 A | 11/1998 | Lubon et al. | 800/2 |
| 5,850,000 A | 12/1998 | Bleck et al. | 800/2 |
| 5,852,224 A | 12/1998 | Cooper et al. | 800/2 |
| 5,914,267 A | 6/1999 | Mertz et al. | 435/320.1 |
| 6,004,805 A | 12/1999 | Casperson | 435/325 |
| 6,011,197 A | 1/2000 | Strelchenko et al. | 800/24 |
| 6,027,722 A | 2/2000 | Hodgson | 424/93.21 |
| 6,066,725 A | 5/2000 | DeBoer et al. | 536/23.5 |
| 6,080,912 A | 6/2000 | Bremel et al. | 800/23 |

FOREIGN PATENT DOCUMENTS

| | | |
|---|---|---|
| EP | 264166 | 8/1996 |
| WO | WO 88/05486 | 7/1988 |
| WO | WO93/03143 | 2/1993 |
| WO | WO 95/17500 | 6/1995 |
| WO | WO 97/07668 | 3/1997 |
| WO | WO 97/07669 | 3/1997 |
| WO | WO99/14310 | 3/1999 |

OTHER PUBLICATIONS

Houdebine. Transgenic Bioreactors. Transgenic Research. 2000, vol. 9, 305-320.*

Houdebine. The Methods to Generate Transgenic Animals and to Control Transgene Expression. Journal of Biotechnology. 2002, vol. 98, pp. 0145-160.*

Alexander and Carey (1999) "Oral IGF-I enhances nutrient and electrolyte absorption in neonatal piglet intestine" Am. J. Physiol Gast. Liv. Phys., 277:G610-G625.

Bleck and Bremel, (1994) "Variation in Expression of a Bovine α-Lactalbumin Transgene in Milk of Transgenic Mice" J. Dairy Sci., 77:1897.

Bleck, GT et al. (1994) "Modification of Milk Composition Using Molecular Biology" Illinois Dairy Report, Department of Animal Sciences, Cooperative Extension Service, Agricultural Experiment Station, College of Agriculture, University of Illinois at Champaign-Urbana, pp. 83-86.

Bleck, G.T. et al. (1995) "Alteration of Milk to Improve Animal Production" Int. Emb. Trans. Soc. Newsletter 13(2):6-10.

Bleck, GT et al. (1996) "Increasing Total Solids and Reducing Lactose and Water Content of Milk" Illinois Dairy Report, Department of Animal Sciences, Cooperative Extension Service, Agricultural Experiment Station, College of Agriculture, University of Illinois at Champaign-Urbana, pp. 89-91.

Bleck et al. (1996) "Production of Transgenic Pigs with Altered Milk to Improve Piglet Growth, Health and Survivability" Illinois Swine Report, Illinois Agricultural Experiment Station, pp. 24-27.

Bleck, GT et al. (Jan. 1, 1996) "Production of Transgenic Swine Containing the Bovine α-Lactalbumin Gene, Theriogenology" 45(1):347.

Bleck et al. (1998) "Production of Bovine α-LAC-Lactalbumin in the Milk of Transgenic Pigs" J. Anim. Sci. 76:(Suppl. 1)/J.Dairy Sci. vol. 81, Supp. 1:219.

Bleck, GT et al (1998) "Production of bovine α-lactalbumin in the milk of transgenic pigs." J. Anim. Sci 76:3072-3078.

Bleck, GT et al (1998) "Transgenic Alteration of Sow Milk to Improve Piglet Growth and Health" University of Illinois Swine Research Reports, pp. 29-30. Sep. 30, 1999.

Bleck, G.T., (1998) Production of transgenic pigs and mice containing the gene encoding human insulin-like growth factor I(IGF-I) under control of the bovine α-lactalbumin promoter and regulatory regions, Denver 1998 ADSA-ASAS Joint Meeting Hosted by Colorado State University, J. Anim. Sci. vol. 76, Suppl. 1/J. Dairy Sci. vol. 81, Suppl 1:213.

Bligh & Cyer (1959) "A Rapid Method of Total Lipid Extraction and Purification" Can. J. Biochem. Phys., 37:911.

Boston, W. Scott et al. (1996) Expression of Bovine α-Lactalbumin in Transgenic Mice Increases Milk Production and Litter Growth, 1996 Illinois Dairy Report, Department of Animal Sciences, Cooperative Extension Service, Agricultural Experiment Station, College of Agriculture, University of Illinois at Champaign-Urbana, 100-101.

Burns et al. (1993) "Vesicular stomatitis virus G glycoprotein pseudotyped retroviral vectors: Concentration to very high titer and efficient gene transfer into mammalian and nonmammalian cells", Proc. Natl. Acad. Sci. USA 90:8033-8037.

Chan et al. (1998) "Transgenic cattle produced by reverse-transcribed gene transfer and Oocytes", PNAS, 95:14028-14033.

Chandrasena et al. (1992) "Expression of Sucrase-Isomaltase mRNA along with Villus-Crypt Axis in the Rat Small Intestine" Cell. Mol. Biol., 38:243-254.

Chomczynski (1993) "A Reagent for the Single-Step Simultaneous Isolation of RNA, DNA and Proteins from Cell and Tissue Samples", Bio Techniques, 15:532.

Cohick (1998) "Role of the Insulin-like Growth Factors and Their Binding Proteins in Lactation" J. Dairy Sci., Symposium: Growth Hormone and Insulin-Like Growth Factors 81:1769-1777.

Donovan et al. (2001) "Transgenic Over-Expression of Bovine α-Lactalbumin and Human Insulin-Like Growth Factor-I in Procine Mammary Gland" J. Dairy Sci. 84(E. Suppl.):E216-E222.

Donovan et al. (1994) "Insulin-Like Growth Factors and Insulin-Like Growth Factor Binding Proteins in Porcine Serum and Milk through Lactation" Pediatric Res., 36:159-168.

Goodman and Schanbacher (1991) "Bovine Lactoferrin mRNA:Sequence*, Analysis, and Expression in the Mammary Gland", Biochem Biophys Res Commun., 180:75-84.

Houle et al. (1997) "Small intestinal disaccharidase activity and ileal villus height are increased in piglets consuming formula containing recombinant human insulin-like growth factor-I", Pediatr. Res., 42:78-86.

Mastromarino et al. (1987) "Characterization of Membrane Components of the Erythrocyte Involved in Vesicular Stomatitis Virus Attachment and Fusion at Acidic pH", J. Gen. Virol. 68:2359-2369.

Monaco, MH, et al. (2000) "Transgenic overexpression of insulin-like growth factor-1 in milk of swine using the bovine α-lactalbumin promoter and regulatory regions" The FASEB Journal Experimental Biology 2000 San Diego, California Apr. 15-18, 2000 Abstracts, FASEB, vol. 14, No. 4, Mar. 15, 2000. pp. A507.

Monaco, MH, et al. (2000) "Transgenic overexpression of insulin-like growth factor-1 in milk of swine using the bovine α-lactalbumin promoter and regulatory regions" The FASEB Journal Experimental Biology 2000, 14:A507, San Diego, California Apr. 15-18, 2000, slides presented at conference.

Monaco, MH, et al. (2000) "Mammary-specific overexpression of IGF-I in transgenic swine increases milk IGF-I and IGF binding protein-2 and -5," 10th International Conference of the International Society for Research Human Milk and Lactation, 2000, (Sep. 15-19, 2000) in Tucson, AZ. Abstract and slide presentation.

Monaco M, Cook JB, Donovan SM, Wheeler MB. (Jan. 2002) Development of swine transgenic for bovine a-lactalbumin and human insulin-like growth factor-I: milk composition, milk production and piglet growth. Theriogenology 57: 784, presented at the International Embryo Transfer Society Meeting in Brazil.

Neuenschwander et al. (1996) "Involution of the Lactating Mammary Gland is Inhibited by the IGF System in a Transgenic Mouse Model", J. Clin. Invest., 97:2225-2232.

Noble MS, Rodriguez-Zas S, Cook JB, Bleck GT, Hurley WL, Wheeler MB. (Apr. 2002) "Lactational performance of first-parity transgenic gilts expressing bovine alpha-lactalbumin in their milk" J Anim Sci. 80(4):1090-6.

Rosfjord and Dickson, (1999) "Growth Factors, Apoptosis, and Survival of Mammary Epithelial Cells" J. Mamm. Gland Biol. Neoplasia, 4:229-237.

Shamay et al. (1988) "Effect of Insulin-Like Growth Factor I on Deoxyribonucleic Acid Synthesis and Galactopoiesis in Bovine Undifferentiated and Lactating Mammary Tissue in Vitro*", Endocrinology, 123:804-808.

Shennan, (1998) "Mammary Gland Membrane Transport Systems" J. Mamm. Gland Biol. Neoplasia, 3:247-258.

Teles, J. (1978) "A Method for Rapid Determination of Lactose"J. Dairy Sci., 61:506-508.

Troelsen et al. (1992) "A Novel Intestinal Trans-factor (NF-LPH1) Interacts with the Lactase-Phlorizin Hydrolase Promoter and Co-varies with the Enzymatic Activity*", J. Biol. Chem., 267:20407-20411.

Tavakkol, et al. (1988) "Porcine Insulin-Like Growth Factor-I (pIGF-I): Complementary Deoxyribonucleic Acid Cloning and Uterine Expression of Messenger Ribonucleic Acid Encoding Evolutionarily Conserved IGF-I Peptides" Molec Endrocrinol. 2:674-681.

Wheeler, et al. (Dec. 2001) "Transgenic alteration of sow milk to improve piglet growth and health" Reproduction Supplement 58:313-324.

Wheeler, et al., (Aug. 17, 1999) Presentation at Transgenic Animal Conference, Tahoe City, CA.

Wheeler, M. (Aug. 1999) Transgenic alteration of sow milk: production and characterization of bovine—lactalbumin and human IGF-I transgenic swine. Abstracts of the Transgenic Animals in Research Conference; Transgenic Research pp. 463; 474-475.

Winder et al. (1989) "Stimulation of DNA synthesis in cultures of ovine mammary epithelial cells by insulin and insulin-like growth factors", J. Endocrinology, 123:319-326.

Houdebine, L.M., The production of pharmaceutical proteins from the milk of transgenic animals. Reprod Nutr Dev (1995) 35, 609-617.

Bleck, G.T., Production of transgenic pigs and mice containing the gene encoding human insulin-like growth factor I(IGF-I) under control of the bovine α-lactalbumin promoter and regulatory regions, Denver 1998 ADSA-ASAS Joint Meeting Hosted by Colorado State University, J. Anim. Sci. vol. 76, Suppl. 1/J. Dairy Sci. vol. 81, Suppl Jan. 1998, pp. 213.

Clark, A.J., The Mammary Gland as a Bioreactor: Expression, Processing, and Production of Recombinant Proteins. Journal of Mammary Gland Biology and Neoplasia. 1998, vol. 3, No. 3, pp. 337-350.

Fujiwara, Y., High-Level Expressing YAC Vector for Transgenic Animal Bioreactors. Molecular Reproduction and Development. 1999, vol. 52, pp. 414-420.

Houdebine, L.M., Transgenic Animal Bioreactors. Transgenic Research. 2000, vol. 9, pp. 305-320.

Bates et al. Mammary Cancer in Transgenic Mice Expressing Insulin-Like Growth Factor-II (IGF-II). British Journal of Cancer 72:1189-1193, 1995.

Daphna-Iken et al. MMTV-Fgf8 Transgenic Mice Develop Mammary and Salivary Gland Neoplasia and Ovarian Stromal Hyperplasia. Oncogene 17:2711-2717, 1998.

Matusi et al. Development of Mammary Hyperplasia and Neoplasia in MMTV-TGF-alpha Transgenic Mice. Cell 61:1147-1155, Jun. 15, 1990.

Brem et al. Expression of Synthetic cDNA Sequences Encoding Humn Insulin-Like Growth Factor-1 (IGF-1) in the Mammary Gland of Transgenic Rabbits. Gene 149:351-355, 1994.

* cited by examiner

SEQ ID NO:1

```
   1  GATCAGTCCTGGGTGGTCATTGAAAGGACTGATGCTGAAGTTGAAGCTCC
  51  AATACTTTGGCCACCTGATGCGAAGAACTGACTCATGTGATAAGACCCTG
 101  ATACTGGGAAAGATTGAAGGCAGGAGGAGAAGGGATGACAGAGGATGGAA
 151  GAGTTGGATGGAATCACCAACTCGATGGACATGAGTTTGAGCAAGCTTCC
 201  AGGAGTTGGTAATGGGCAGGGAAGCCTGGCGTGCTGCAGTCCATGGGGTT
 251  GCAAAGAGTTGGACACTACTGAGTGACTGAACTGATAGTGTAATC
 301  CATGGTACAGAATATAGGATAAAAAGAGGAAGAGTTTGCCCTGATTCTG
 351  AAGAGTTGTAGGATATAAAAGTTTAGAATACCTTTAGTTTGGAAGTCTTA
 401  AATTATTTACTTAGGATGGGTACCCACTGCAATATAAGAAATCAGGCTTT
 451  AGAGACTGATGTAGAGAGAATGAGCCCTGGCATACCAGAAGCTAACAGCT
 501  ATTGGTTATAGCTGTTATAACCAATATATAACCAATATATTGGTTATATA
 551  GCATGAAGCTTGATGCCAGCAATTTGAAGGAACCATTTAGAACTAGTATC
 601  CTAAACTCTACATGTTCCAGGACACTGATCTTAAAGCTCAGGTTCAGAAT
 651  CTTGTTTTATAGGCTCTAGGTGTATATTGTGGGGCTTCCCTGGTGGCTCA
 701  GATGGTAAAGTGTCTGCCTGCAATGTGGGTGATCTGGGTTCGATCCCTGG
 751  CTTGGGAAGATCCCCTGGAGAAGGAAATGGCAACCCACTCTAGTACTCTT
 801  ACCTGGAAAATTCCATGGACAGAGGAGCCTTGTAAGCTACAGTCCATGGG
 851  ATTGCAAAGAGTTGAACACAACTGAGCAACTAAGCACAGCACAGTACAGT
 901  ATACACCTGTGAGGTGAAGTGAAGTGAAGGTTCAATGCAGGGTCTCCTGC
 951  ATTGCAGAAAGATTCTTTACCATCTGAGCCACCAGGGAAGCCCAAGAATA
1001  CTGGAGTGGGTAGCCTATTCCTTCTCCAGGGGATCTTCCCATCCCAGGAA
1051  TTGAACTGGAGTCTCCTGCATTTCAGGTGGATTCTTCACCAGCTGAACTA
1101  CCAGGTGGATACTACTCCAATATTAAAGTGCTTAAAGTCCAGTTTTCCCA
1151  CCTTTCCCAAAAAGGTTGGGTCACTCTTTTTTAACCTTCTGTGGCCTACT
1201  CTGAGGCTGTCTACAAGCTTATATATTTATGAACACATTTATTGCAAGTT
1251  GTTAGTTTTAGATTTACAATGTGGTATCTGGCTATTTAGTGGTATTGGTG
1301  GTTGGGGATGGGGAGGCTGATAGCATCTCAGAGGGCAGCTAGATACTGTC
1351  ATACACACTTTTCAAGTTCTCCATTTTTGTGAAATAGAAAGTCTCTGGAT
1401  CTAAGTTATATGTGATTCTCAGTCTCTGTGGTCATATTCTATTCTACTCC
1451  TGACCACTCAACAAGGAACCAAGATATCAAGGGACACTTGTTTTGTTTCA
1501  TGCCTGGGTTGAGTGGGCCATGACATATGATGATGTACAGTCCTTTTCCA
1551  TATTCTGTATGTCTCTAAGAGGAAGGAGGAGTTGGCCGTGGACCCTTTGT
1601  GCATTTTCTGATTGCTTCACTTGTATTACCCCTGAGGCCCCCTTTGTTCC
1651  TGAAATAGGTTGGGCACATCTTGCTTCCTAGAACCAACACTACCAGAAAC
1701  AACATAAATAAAGCCAAATGGGAACAGGATCATGTTTGTAACACTCTTT
1751  GGGCAGGTAACAATACCTAGTATGGACTAGAGATTCTGGGGAGGAAAGGA
1801  AAAGTGGGGTGAAATTACTGAAGGAAGCTCAATGTTTCTTTGTTGGTTTT
1851  ACTGGCCTCTCTTGTCATCCTCTTCCTGGATGTAAGGCTTGATGCCAGGG
1901  CCCCTAAGGCTTTTTCCACAAATAAAAGGAGGTGAGCAGTGTGGTGACCC
1951  CATTTCAGAATCTTGAGGGGTAACGAATTCTAACCAAAATGATGTCCTTT
2001  GTCTCTCTGCTCCTGGTAGGAATCCTATTCCATGCCACCCAGGCTGGACC
2051  GGAGACGCTCTGCGGGCTGAGCTGGTGGATGCTCTTCAGTTCGTGTGTG
2101  GAGACAGGGGATTTTATTTCAACAAGCCCACAGGGTATGGATCCAGCAGT
2151  CGGAGGGCGCCCCAGACAGGCATCGTGGATGAGTGCTGCTTCCGGAGCTG
2201  TGATCTAAGGAGGCTGGAGATGTATTGCGCACCCCTAAAGCCTGCCAAGT
```

Figure 3 - 1

```
2251 CAGCTTGATAGCTCGACGGATCCCCAAAATGTGAGGTGTTCCGGGAGCTG
2301 AAAGACTTGAAGGGCTACGGAGGTGTCAGTTTGCCTGAATGTGAGTTCCC
2351 TGCTATTTTGCTTTGTCCATAATTCATCCTCTTCACTCTTTCCCTCCAT
2401 TCTCTTCATCCTCTTTTCCCCTCTACTTTTAATTATCAAACAATTCTCT
2451 TATTTGTTTACTCTTTTATTACATTTATTTATCTGCCTCTCCTTTTTCCC
2501 ATTGTCTGATCCTTTGGAACTCTTTTCACCTTAACAAGATACTCTGTGGT
2551 CTGCCATATTTGGAGATTGGTTGGAGAGCCTTTTTCGGTCTGGGAATACA
2601 GGTCCTCATTTATGCTATACATGAACATCCTTGTGAAATCTCTTTTTCGT
2651 CTTTCTTTCAGGGGTCTGTACCGCGTTTCATACCAGTGGTTATGACACAC
2701 AAGCCATAGTACAAAACAATGACAGCACAGAATATGGACTCTTCCAGATA
2751 AATAATAAAATTTGGTGCAAAGACGACCAGAACCCTCACTCAAGCAACAT
2801 CTGTAACATCTCCTGTGACAGTGAGTAACTTCTTTTTACTCTGTTCCTGT
2851 GTTTTCTGAAACCTACTCCTGGGATAACCTCCTTTTTTTTGGTGTGAAG
2901 CACACCTCTGGCTTCACTGCCTTGGACTCCAAATTAACTGTGGGACTTGA
2951 TAATACCGAGTAAGAGGCTCTTAGAATTTTTCATTAACACTAAATCCCCA
3001 GACAGTTTCTTAAAGTTCCTGGGTAGGTGACCTGAGCTGTTTGGGGATCT
3051 TGATGTATAATACCCTGTATTTTCAGACTAAGTTGGTTGATGAAGTTGAT
3101 AATTCCTAAGGAGCTGCCCCAGAGAAGAGAAGGGAGTCCTTACCTAGGGA
3151 TAGGCATTACTGTATTAAATTTCTCACCCAGAAGGCAACAGGCATAAGCC
3201 TCTAGTTCAGAGAAAACCAGAGAAGAGGGAAATTCATTATCCTTCTGGGT
3251 AATACTTAGCTCTCTCATTTTTTCCACCAGAGGCTCCTGCCAGAGTTCCT
3301 GGATGATGATCTTACTGATGACATTATGTGTGTCAAGAAGATTCTGGATA
3351 AAGTAGGAATTAACTACTGGTGAGTCACCTCTCTATTTTTCACTTAATCT
3401 TTCCTCTCTTTCTTCTCAGTCCTTTCGTCCCAGCACTATACTCCTTTCTC
3451 TCTATTTCTTGGTCTTTTAAGCTAGAATGTAATCTTAAAAACAAAAATCA
3501 TCAAGCAGACTCCGGTTTCCAATTTTGAAGCTTCACTTACTTCACTCCCG
3551 TTAGCAATTTTCCTACCTAAGGGTCCCTAATAGAGGGCTGAGATCCAGGA
3601 TTTCCTTCACCAGGACTTGAACATCTAATTCTACTTGTTCAGTCCTACAT
3651 CCTAAGGCACGCCCTTTGACCACTGCCCCGCAATTTTCTTGGAGTTTTAA
3701 AAAATGGACCTTACTCCACTAAGTGGCTCAGTGTCTCTAGCCATGTGGCT
3751 AGGAAAGTCTGTCTGTAATTTTAACCCACAGTCTTCCACCTCAGCCTTCC
3801 TGGGGATAAAGCTAGATGTAAATCTAACCAAGATCCTGTCAGTAATTTGC
3851 CTTGTCTCCTTCTTCATGATCAGGTTGGCCCATAAAGCACTCTGTTCTGA
3901 GAAGCTGGATCAGTGGCTCTGTGAGAAGTTGTGAACACCTGCTGTCTTTG
3951 CTGCTTCTGTCCTCTTTCTGTTCCTGGAACTCCTCTGCCCCGTGGCTACC
4001 TCGTTTTGCTTCTTTGTACCCCCTTGAAGCTAACTCGTCTCTGAGCCCTG
4051 GGCCCTGTAGTGACAATGGACATGTAAGGACTAATCTCCAGGTGTGCATG
4101 AATGGCGCTCTGGACTTTTGACCCTTGCTCGATGTCCCTGATGGCGCTTT
4151 TAATGCAACAGTACATATTCCACTTTTGTCCCGAATAAAAAGCCTGATTT
4201 TGAGTGGCTGGCTGTATTTTCTTCCTGGTGGGAGAGGGAGGAAATAGGGT
4251 GAGTAGGTAGACCTGGCCATGGGTCACAGACCCCTTCATCTCTACTAAAG
4301 AGGATAGAGAGGCTGAACTTATAACAACTCAAAGATGGAGATTACTTTCT
4351 GTATTAATTCAATTCAACAGAGTTTATTGATCACCTAGCATAATTTAAA
4401 GAGCTATGGAGGGATCTAAAGTTGACTAAAAGCATCTCTTACCTAAACT
4451 GCTGCTAAGTCACTTCAGTTGTGTCCGACTCTGTGTGACCCCATAGACGG
4501 TAGCCCACAAGGCTCCCATGTCCCTGGAATTC
```

Figure 3 - 2

| Range | Description |
|---|---|
| 1-1951 | Bovine a-Lactalbumin 5' Flanking Region/Promoter Region |
| 1952 | Bovine -Lactalbumin Transcription Start Point |
| 1989-2045 | Bovine a-Lactalbumin Signal Peptide Coding Region |
| 2046-2255 | Human/Bovine/Porcine IGF-I Coding Region |
| 2256-2258 | IGF-I Stop Codon |
| 2259-2340 | Cloning Sites and Bovine a-Lactalbumin 3' End of Exon 1 |
| 2341-2661 | Bovine a-Lactalbumin Intron 1 |
| 2662-2820 | Bovine a-Lactalbumin Exon 2 |
| 2821-3294 | Bovine a-Lactalbumin Intron 2 |
| 3295-3369 | Bovine a-Lactalbumin Exon 3 |
| 3370-3873 | Bovine a-Lactalbumin Intron 3 |
| 3874-4203 | Bovine a-Lactalbumin Exon 4 |
| 4204-4532 | Bovine a-Lactalbumin 3' Flanking Region |

SEQ ID NO:2

```
1    GGACCGGAGACGCTCTGCGGGGCTGAGCTGGTGGATGCTCTTCAGTTCGT
51   GTGTGGAGACAGGGGATTTTATTTCAACAAGCCCACAGGGTATGGATCCA
101  GCAGTCGGAGGGCGCCCCAGACAGGCATCGTGGATGAGTGCTGCTTCCGG
151  AGCTGTGATCTAAGGAGGCTGGAGATGTATTGCGCACCCCTAAAGCCTGC
201  CAAGTCAGCT
```

Figure 3 - 3

* York-Duroc cross-bred sows (Donovan et al. *Pediatric Research* 1994; 36:159-163)

US 7,169,963 B2

MAMMALS EXPRESSING IGF-1 AND ALPHA-LACTALBUMIN IN THEIR MILK

CROSS-REFERENCE TO RELATED APPLICATIONS

This application is a divisional of application Ser. No. 09/930,377, filed Aug. 15, 2001, now U.S. Pat. No. 6,677,500 which claims the benefit of U.S. Provisional Application No. 60/225,474, filed Aug. 15, 2000, which are incorporated by reference in their entirety to the extent not inconsistent with the disclosure herewith.

STATEMENT REGARDING FEDERALLY SPONSORED RESEARCH OR DEVELOPMENT

This invention was made with Government support under Contract No. 96-35206-3850 awarded by the U.S. Department of Agriculture. The Government has certain rights in this invention.

FIELD OF THE INVENTION

The present invention relates to animals that express exogenous growth factors in their milk, and in particular to pigs that express exogenous IGF-I in their milk. The present invention also relates to methods for increasing piglet weight gain and intestinal lactase enzyme activity.

BACKGROUND OF THE INVENTION

The early neonatal period is the time of greatest animal loss for pork producers. The 1991 USDA National Swine Survey on Morbidity/Mortality and Heath Management of Swine in the U.S. estimated that overall pre-weaning mortality was 15% and that nearly all cases of morbidity and mortality occurred in piglets less than 7 days of age (USDA, 1991). Importantly, 58% of the cases of morbidity were reportedly due to scours and 30% of the mortality was attributed to scours or starvation.

In recent years, pork producers have reduced lactation lengths in an attempt to maximize the number of piglets born per sow per year. Lactation periods of 10–14 days are common in the swine industry. This production system creates a need for sows that produce high levels of milk in early lactation in order to obtain maximal piglet growth. In addition, the number of piglets born per litter has increased, thus adding to the demand for higher milk production early in lactation.

Low milk production is manifested by slow piglet growth before weaning and suboptimal growth post-weaning (Hartman et al., Symp. Zool. Sci., 51:301 [1984]). Milk production accounts for 44% of the growth weight of the piglets (Lewis et al., J. Anim. Sci., 47:634 [1978]). In addition, gastrointestinal disease in piglets reduces their survival. Such diseases are typically treated with antibiotics. It has also been suggested that bioactive substances in milk may have important functions in piglet growth and health.

Clearly, the industry would benefit from a method of increasing milk production and nutrient value in sow milk. Supplementing milk with growth factors or nutrients is too costly and labor-intensive to be a viable solution. The art is in need of a cost effective method of increasing milk production and nutrient value in lactating sows.

SUMMARY OF THE INVENTION

The present invention relates to animals that express exogenous growth factors in their milk, and in particular to pigs that express exogenous IGF-I in their milk. The present invention also relates to methods for increasing piglet weight gain and intestinal lactase enzyme activity.

In some embodiments, the present invention provides a transgenic animal having a genome comprising a heterologous nucleic acid sequence encoding a growth factor operably linked to a mammary preferential promoter, wherein descendants of the transgenic animal express an increased amount of growth factor in their milk as compared to control non-transgenic animals. The present invention is not limited to any particular growth factor or source of the nucleic acid encoding the growth factor. Indeed, a variety of growth factors are contemplated, including, but not limited to insulin-like growth factor I, insulin-like growth factor II, epidermal growth factor, platelet derived growth factor, fibroblast growth factor, and transforming growth factor. The present invention is not limited to any particular transgenic animal. Indeed, a variety of transgenic animals are contemplated, including, but not limited to ungulates such as pigs, cattle, sheep, and goats. The animal may be nonhuman. The present invention is not limited to any particular gender of transgenic animal. Indeed, both male and female transgenic animals are contemplated. The present invention is not limited to any particular IGF-I gene. Indeed, a variety of IGF-I genes are contemplated, including, but not limited to human, porcine, and bovine insulin-like growth factor I genes. In some particularly preferred embodiments, the insulin-like growth factor I comprises SEQ ID NO:2. In other preferred embodiments, the heterologous nucleic acid sequence is encoded by SEQ ID NO:1. The present invention is not limited to any particular mammary preferential promoter or source of the nucleic acid encoding the promoter. Indeed, a variety of mammary preferential promoters are contemplated, including, but not limited to alpha-lactalbumin promoters, whey acidic protein promoters, and casein promoters. In some embodiments, the gametes of said transgenic animal comprise said heterologous nucleic acid sequence. When the animal is a heterozygote, it is understood that only a portion of the gametes will comprise the transgene.

In other embodiments, the present invention provides compositions comprising milk from a transgenic animal having a genome comprising a heterologous nucleic acid sequence encoding a growth factor operably linked to a mammary preferential promoter, wherein said milk comprises an increased amount of growth factor as compared to milk from control non-transgenic animals. The present invention is not limited to any particular growth factor or the particular source of the nucleic acid sequence encoding the growth factor. Indeed, a variety of growth factors are contemplated, including, but not limited to insulin-like growth factor I, insulin-like growth factor II, epidermal growth factor, platelet derived growth factor, fibroblast growth factor, and transforming growth factor. The present invention is not limited to any particular transgenic animal. Indeed, a variety of transgenic animals are contemplated, including, but not limited to ungulates such as pigs, cattle, sheep, and goats. The animal may be non-human. The present invention is not limited to any particular gender of transgenic animal. Indeed, both male and female transgenic animals are contemplated. The present invention is not limited to any particular IGF-I gene or the particular source of the nucleic acid encoding the growth factor. Indeed, a variety of IGF-I genes are contemplated, including, but not limited to human, porcine, and bovine insulin-like growth factor I genes. In some particularly preferred embodiments, the insulin-like growth factor I comprises SEQ ID NO:2. In other preferred embodiments, the heterologous nucleic acid sequence is encoded by SEQ ID NO:1. The present invention is not limited to any particular mammary preferential promoter or the particular source of the nucleic acid encoding the promoter. Indeed, a variety of mammary preferential promoters are contemplated, including, but not limited to alpha-lactalbumin promoters, whey acidic protein promoters, and casein promoters.

In still further embodiments, the present invention provides methods for increasing weight gain in a suckling animal, comprising: a) providing i) a transgenic animal having a genome comprising a heterologous nucleic acid sequence encoding a growth factor gene operably linked to a mammary preferential promoter, wherein the transgenic animal expresses an increased amount of growth factor in its milk as compared to control non-transgenic animals; and ii) a suckling offspring of the transgenic animal; and b) providing the suckling offspring milk of said transgenic animal, wherein the suckling offspring has increased weight gain relative to a suckling offspring provided milk of a non-transgenic animal. The present invention is not limited any particular growth factor or the particular source of the nucleic acid encoding the growth factor. Indeed, a variety of growth factors are contemplated, including, but not limited to insulin-like growth factor I, insulin-like growth factor II, epidermal growth factor, platelet-derived growth factor, fibroblast growth factor, and transforming growth factor. The present invention is not limited to any particular transgenic animal. Indeed, a variety of transgenic animals are contemplated, including, but not limited to ungulates such as pigs, cattle, sheep, and goats. The animal may be non-human. The present invention is not limited to any particular gender of transgenic animal. Indeed, both male and female transgenic animals are contemplated. Likewise, in preferred embodiments, the suckling animal can be a piglet, calf, lamb, or kid. The present invention is not limited to any particular IGF-I gene or the particular source of the nucleic acid encoding the growth factor. Indeed, a variety of IGF-I genes are contemplated, including, but not limited to human, porcine, and bovine insulin-like growth factor I genes. In some particularly preferred embodiments, the insulin-like growth factor I comprises SEQ ID NO:2. In other preferred embodiments, the heterologous nucleic acid sequence is encoded by SEQ ID NO:1. The present invention is not limited to any particular mammary preferential promoter or the particular source of the nucleic acid encoding the promoter. Indeed, a variety of mammary preferential promoters are contemplated, including, but not limited to alpha-lactalbumin promoters, whey acidic protein promoters, and casein promoters.

In still other embodiments, the present invention provides methods for increasing intestinal lactase activity in a suckling animal, comprising: a) providing i) a transgenic animal having a genome comprising a heterologous nucleic acid sequence encoding a growth factor operably linked to a mammary preferential promoter, wherein the transgenic animal expresses an increased amount of growth factor in its milk as compared to control non-transgenic animals; and ii) a suckling offspring of the transgenic animal; and b) providing the suckling offspring milk of the transgenic animal, wherein the suckling offspring has increased intestinal lactase activity relative to a suckling offspring provided milk of a non-transgenic animal. The present invention is not limited any particular growth factor or the particular source of the nucleic acid encoding the growth factor. Indeed, a variety of growth factors are contemplated, including, but not limited to insulin-like growth factor I, insulin-like growth factor II, epidermal growth factor, platelet-derived growth factor, fibroblast growth factor, and transforming growth factor. The present invention is not limited to any particular transgenic animal. Indeed, a variety of transgenic animals are contemplated, including, but not limited to ungulates such as pigs, cattle, sheep, and goats. The animal may be non-human. The present invention is not limited to any particular gender of transgenic animal. Indeed, both male and female transgenic animals are contemplated. Likewise, in preferred embodiments, the suckling animal can be a piglet, calf, lamb, or kid. The present invention is not limited to any particular IGF-I gene or the particular source of the nucleic acid encoding the growth factor. Indeed, a variety of IGF-I genes are contemplated, including, but not limited to human, porcine, and bovine insulin-like growth factor I genes. In some particularly preferred embodiments, the insulin-like growth factor I comprises SEQ ID NO:2. In other preferred embodiments, the heterologous nucleic acid sequence is encoded by SEQ ID NO:1. The present invention is not limited to any particular mammary preferential promoter or the particular source of the nucleic acid encoding the promoter. Indeed, a variety of mammary preferential promoters are contemplated, including, but not limited to alpha-lactalbumin promoters, whey acidic protein promoters, and casein promoters.

In some embodiments, the present invention provides methods for increasing intestinal cell division in a suckling animal, comprising: a) providing i) a transgenic animal having a genome comprising a heterologous nucleic acid sequence encoding a growth factor operably linked to a mammary preferential promoter, wherein the transgenic animal expresses an increased amount of growth factor in its milk as compared to control non-transgenic animals; and ii) a suckling offspring of the transgenic animal; and b) providing the suckling offspring milk of the transgenic animal, wherein the suckling offspring has increased intestinal cell division relative to a suckling offspring provided milk of a non-transgenic animal. The present invention is not limited any particular growth factor or the particular source of the nucleic acid encoding the growth factor. Indeed, a variety of growth factors are contemplated, including, but not limited to insulin-like growth factor I, insulin-like growth factor II, epidermal growth factor, platelet derived growth factor, fibroblast growth factor, and transforming growth factor. The present invention is not limited to any particular transgenic animal. Indeed, a variety of transgenic animals are contemplated, including, but not limited to ungulates such as pigs, cattle, sheep, and goats. The animal may be non-human. The present invention is not limited to any particular gender of transgenic animal. Indeed, both male and female transgenic animals are contemplated. Likewise, in preferred embodiments, the suckling animal can be a piglet, calf, lamb, or kid. The present invention is not limited to any particular IGF-I gene. Indeed, a variety of IGF-I genes are contemplated, including, but not limited to human, porcine, and bovine insulin-like growth factor I genes. In some particularly preferred embodiments, the insulin-like growth factor I comprises SEQ ID NO:2. In other preferred embodiments, the heterologous nucleic acid sequence is encoded by SEQ ID NO:1. The present invention is not limited to any particular mammary preferential promoter or the particular source of the nucleic acid encoding the growth factor. Indeed, a variety of mammary preferential promoters are contemplated, including, but not limited to alpha-lactalbumin promoters, whey acidic protein promoters, and casein promoters.

In other embodiments, the present invention provides methods for increasing intestinal villi length in a suckling animal, comprising: a) providing i) a transgenic animal having a genome, said genome comprising a heterologous nucleic acid sequence encoding a growth factor operably linked to a mammary preferential promoter, wherein the transgenic animal expresses an increased amount of growth factor in its milk as compared to control non-transgenic animals; and ii) a suckling offspring of the transgenic animal; and b) providing the suckling offspring milk of said transgenic animal, wherein the suckling offspring has increased intestinal villi length relative to a suckling offspring provided milk of a non-transgenic animal. The present invention is not limited any particular growth factor or the particular source of the nucleic acid encoding the growth factor. Indeed, a variety of growth factors are contemplated, including, but not limited to insulin-like growth factor I, insulin-like growth factor II, epidermal growth factor, platelet derived growth factor, fibroblast growth factor, and transforming growth factor. The present invention is not limited to any particular transgenic animal. Indeed, a variety of transgenic animals are contemplated, including, but not limited to ungulates such as pigs, cattle, sheep, and goats. The animal may be non-human. The present invention is not limited to any particular gender of transgenic animal. Indeed, both male and female transgenic animals are contemplated. Likewise, in preferred embodiments, the suckling animal can be a piglet, calf, lamb, or kid. The present invention is not limited to any particular IGF-I gene. Indeed, a variety of IGF-I genes are contemplated, including, but not limited to human, porcine, and bovine insulin-like growth factor I genes. In some particularly preferred embodiments, the insulin-like growth factor I comprises SEQ ID NO:2. In other preferred embodiments, the heterologous nucleic acid sequence is encoded by SEQ ID NO:1. The present invention is not limited to any particular mammary preferential promoter or the particular source of the nucleic acid encoding the growth factor. Indeed, a variety of mammary preferential promoters are contemplated, including, but not limited to alpha-lactalbumin promoters, whey acidic protein promoters, and casein promoters.

In some embodiments, the present invention provides methods for increasing resistance to intestinal pathogens in a suckling animal, comprising: a) providing i) a transgenic animal having a genome comprising a heterologous nucleic acid sequence encoding a growth factor operably linked to a mammary preferential promoter, wherein the transgenic animal express an increased amount of growth factor in their milk as compared to control non-transgenic animals; ii) a suckling offspring of the transgenic animal; and b) providing the suckling offspring milk of said transgenic animal, wherein the suckling offspring has increased resistance to intestinal parasites relative to a suckling offspring provided milk of a non-transgenic animal. The present invention is not limited any particular growth factor or the particular source of the nucleic acid encoding the growth factor. Indeed, a variety of growth factors are contemplated, including, but not limited to insulin-like growth factor I, insulin-like growth factor II, epidermal growth factor, platelet derived growth factor, fibroblast growth factor, and transforming growth factor. The present invention is not limited to any particular transgenic animal. Indeed, a variety of transgenic animals are contemplated, including, but not limited to ungulates such as pigs, cattle, sheep, and goats. The animal may be non-human. The present invention is not limited to any particular gender of transgenic animal. Indeed, both male and female transgenic animals are contemplated. Likewise, in preferred embodiments, the suckling animal can be a piglet, calf, lamb, or kid. The present invention is not limited to any particular IGF-I gene. Indeed, a variety of IGF-I genes are contemplated, including, but not limited to human, porcine, and bovine insulin-like growth factor I genes. In some particularly preferred embodiments, the insulin-like growth factor I comprises SEQ ID NO:2. In other preferred embodiments, the heterologous nucleic acid sequence is encoded by SEQ ID NO:1. The present invention is not limited to any particular mammary preferential promoter or the particular source of the nucleic acid encoding the promoter. Indeed, a variety of mammary preferential promoters are contemplated, including, but not limited to alpha-lactalbumin promoters, whey acidic protein promoters, and casein promoters. The present invention is not limited to resistance to any particular pathogen. Indeed, resistance to a variety of pathogens is contemplated, including, but not limited to rotovirus, coronavirus, *E. coli*, and *Salmonella*.

In some embodiments, the present invention provides a transgenic animal having a genome comprising a nucleic acid sequence encoding a growth factor and encoding alpha-lactalbumin operably linked to a mammary preferential promoter, said animal expressing an increased amount of growth factor and an increased amount of alpha-lactalbumin in its milk as compared to control non-transgenic animals.

In other embodiments, the present invention provides a transgenic animal having a genome comprising a nucleic acid sequence encoding a growth factor and encoding alpha-lactalbumin operably linked to a mammary preferential promoter, said animal expressing an increased amount of growth factor in its milk and an increased milk volume as compared to control non-transgenic animals.

In other embodiments, the present invention provides a method of increasing the volume of milk and the growth factor content of milk in transgenic animals, said method comprising: providing a transgenic animal having a genome, said genome comprising a heterologous nucleic acid sequence encoding a growth factor gene and encoding alpha-lactalbumin operably linked to a mammary preferential promoter, wherein said transgenic animal expresses an increased amount of growth factor in its milk and an increased milk volume as compared to control non-transgenic animals.

DESCRIPTION OF THE FIGURES

FIG. 3 shows the nucleic acid sequences of SEQ ID NOs: 1 and 2.

DEFINITIONS

Figure 1:
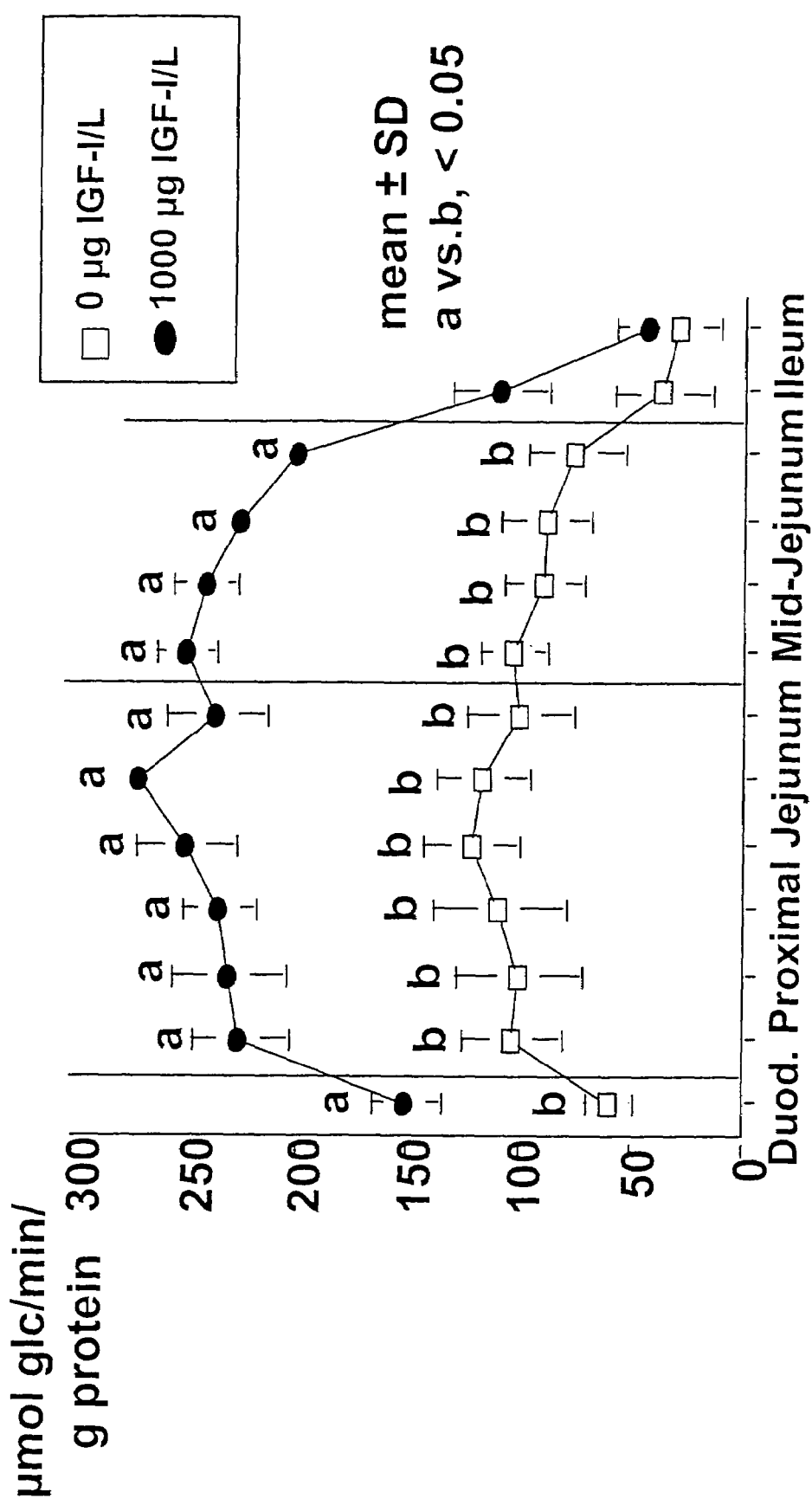
FIG. 1 shows lactase activity in various intestinal segments in piglets fed 1.0 mg/L IGF-I for 14 days and control piglets.

To facilitate understanding of the invention, a number of terms are defined below.

As used herein, the term "host cell" refers to any eukaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the term "integrated" refers to a vector that is stably inserted into the genome (i.e., into a chromosome) of a host cell.

As used herein, the term "genome" refers to the genetic material (e.g., chromosomes) of an organism.

As used herein the term "suckling offspring" refers to an animal that is nursing a female of its species. The term "suckling offspring" includes both progeny of a female animal as well as sucklings that have been grafted onto the female animal.

As used herein, the term "mammary preferential promoter" refers to a promoter that preferentially causes the expression of a gene in the mammary gland. Different "mammary preferential promoters" can effect different expression profiles to a gene (e.g., exhibiting different expression levels at different times during lactation). "Mammary preferential promoters" include those that effect high expression levels at different stages of lactation, including early lactation (e.g., the human alpha-lactalbumin promoter). Examples of mammary specific promoters include, but are not limited to alpha-lactalbumin promoters, whey acidic protein promoters, alpha-, beta- and kappa-casein promoters, and lactoferrin promoters. The term "mammary preferential promoters" encompasses mammary preferential promoters from all mammalian species (e.g., human, mouse, bovine, porcine, and ovine mammary preferential promoters.) Furthermore, the term "mammary preferential promoter" encompasses variants of the wild-type promoters.

The term "nucleotide sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.). A "nucleic acid sequence of interest" may be a derived from the host organism or cell or may be a "heterologous nucleic acid sequence."

As used herein, the terms "heterologous nucleic acid sequence," "heterologous gene" or "exogenous gene" refer to a nucleic acid sequence (e.g., a gene) that is not naturally present in a host organism or cell, or is artificially introduced into a host organism or cell.

As used herein, the term "protein of interest" refers to a protein encoded by a nucleic acid of interest.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring or synthetic protein molecule, "amino acid sequence" and like terms, such as "polypeptide" or "protein" are not meant to limit the amino acid sequence to the complete, native amino acid sequence associated with the recited protein molecule.

As used herein, the terms "nucleic acid molecule encoding," "nucleic acid sequence encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

As used herein, the term "variant," when used in reference to a protein, refers to proteins encoded by partially homologous nucleic acids so that the amino acid sequence of the proteins varies. As used herein, the term "variant" encompasses proteins encoded by homologous genes having conservative amino acid substituations, nonconservative amino acid substituations, or both that do not result in a change in protein function, as well as proteins encoded by homologous genes having amino acid substituations that cause decreased (e.g., null mutations) protein function or increased protein function.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "homology" and "percent identity" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×

SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "selectable marker" refers to a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with $tk^-$ cell lines, the CAD gene which is used in conjunction with CAD-deficient cells and the mammalian hypoxanthine-guanine phosphoribosyl transferase (hprt) gene which is used in conjunction with $hprt^-$ cell lines. A review of the use of selectable markers in mammalian cell lines is provided in Sambrook, J. et al., *Molecular Cloning: A Laboratory Manual,* 2nd ed., Cold Spring Harbor Laboratory Press, New York (1989) pp. 16.9–16.15.

As used herein, the term "regulatory element" refers to a genetic element which controls some aspect of the expression of nucleic acid sequences. For example, a promoter is a regulatory element that facilitates the initiation of transcription of an operably linked coding region. Other regulatory elements are splicing signals, secretion signal sequences, polyadenylation signals, termination signals, RNA export elements, internal ribosome entry sites, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, Voss et al., Trends Biochem. Sci., 11:287 [1986]; and Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor la gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques such as cloning and recombination) such that transcription of that gene is directed by the linked enhancer/promoter.

As used herein, the term "secretion signal" refers to any DNA sequence that when operably linked to a recombinant DNA sequence encodes a signal peptide which is capable of causing the secretion of the recombinant polypeptide. In general, the signal peptides comprise a series of about 15 to 30 hydrophobic amino acid residues (See, e.g., Zwizinski et al., J. Biol. Chem. 255(16): 7973–77 [1980], Gray et al., Gene 39(2): 247–54 [1985], and Martial et al., Science 205: 602–607 [1979]). Such secretion signal sequences are preferably derived from genes encoding polypeptides secreted from the cell type targeted for tissue-specific expression (e.g., secreted milk proteins such as alpha-lactalbumin, alpha-, beta-, and kappa-casein, and whey acidic protein for expression in and secretion from mammary secretory cells). Secretory DNA sequences, however, are not limited to such sequences. Secretory DNA sequences from proteins secreted from many cell types and organisms may also be used (e.g., the secretion signals for t-PA, serum albumin, lactoferrin, and growth hormone, and secretion signals from microbial genes encoding secreted polypeptides such as from yeast, filamentous fungi, and bacteria).

Regulatory elements may be tissue specific or cell specific. The term "tissue specific" as it applies to a regulatory element refers to a regulatory element that is capable of directing greater levels of expression of a nucleotide sequence of interest in a specific type of tissue (e.g., liver) relative to the level of expression of the same nucleotide sequence of interest in a different type of tissue (e.g., lung).

Tissue specificity of a regulatory element may be evaluated by, for example, operably linking a reporter gene to a promoter sequence (which is not tissue-specific) and to the regulatory element to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the regulatory element is "specific" for the tissues in which greater levels of expression are detected. Thus, the term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute" tissue-specific expression is meant to indicate expression in a single tissue type (e.g., liver) with no detectable expression in other tissues.

The term "cell type specific" as applied to a regulatory element refers to a regulatory element which is capable of directing a greater level of expression of a nucleotide sequence of interest in a specific type of cell relative to the level of expression of the same nucleotide sequence of interest in a different type of cell within the same tissue. The term "cell type specific" when applied to a regulatory element also means a regulatory element capable of promoting selective expression of a nucleotide sequence of interest in a region within a single tissue.

Cell type specificity of a regulatory element may be assessed using methods well known in the art (e.g., immunohistochemical staining and/or Northern blot analysis). Briefly, for immunohistochemical staining, tissue sections are embedded in paraffin, and paraffin sections are reacted with a primary antibody specific for the polypeptide product encoded by the nucleotide sequence of interest whose expression is regulated by the regulatory element. A labeled (e.g., peroxidase conjugated) secondary antibody specific for the primary antibody is allowed to bind to the sectioned tissue and specific binding detected (e.g., with avidin/biotin) by microscopy. Briefly, for Northern blot analysis, RNA is isolated from cells and electrophoresed on agarose gels to fractionate the RNA according to size followed by transfer of the RNA from the gel to a solid support (e.g., nitrocellulose or a nylon membrane). The immobilized RNA is then probed with a labeled oligo-deoxyribonucleotide probe or DNA probe to detect RNA species complementary to the probe used. Northern blots are a standard tool of molecular biologists.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one which is capable of directing a level of transcription of an operably linked nucleic acid sequence in the presence of a stimulus (e.g., heat shock, chemicals, etc.) which is different from the level of transcription of the operably linked nucleic acid sequence in the absence of the stimulus.

The presence of "splicing signals" on an expression vector often results in higher levels of expression of the recombinant transcript. Splicing signals mediate the removal of introns from the primary RNA transcript and consist of a splice donor and acceptor site (Sambrook et al., *Molecular Cloning: A Laboratory Manual,* 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6–16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell). However, it is not intended that expression vectors be limited to any particular viral origin of replication.

As used herein, the term "long terminal repeat" of "LTR" refers to transcriptional control elements located in or isolated from the U3 region 5' and 3' of a retroviral genome. As is known in the art, long terminal repeats may be used as control elements in retroviral vectors, or isolated from the retroviral genome and used to control expression from other types of vectors.

As used herein, the term "secretion signal" refers to any DNA sequence which when operably linked to a recombinant DNA sequence encodes a signal peptide which is capable of causing the secretion of the recombinant polypeptide. In general, the signal peptides comprise a series of about 15 to 30 hydrophobic amino acid residues (See, e.g., Zwizinski et al., J. Biol. Chem. 255(16): 7973–77 [1980], Gray et al., Gene 39(2): 247–54 [1985], and Martial et al., Science 205: 602–607 [1979]). Such secretion signal sequences are preferably derived from genes encoding polypeptides secreted from the cell type targeted for tissue-specific expression (e.g., secreted milk proteins for expression in and secretion from mammary secretory cells). Secretory DNA sequences, however, are not limited to such sequences. Secretory DNA sequences from proteins secreted from many cell types and organisms may also be used (e.g., the secretion signals for t-PA, serum albumin, lactoferrin, and growth hormone, and secretion signals from microbial genes encoding secreted polypeptides such as from yeast, filamentous fungi, and bacteria).

As used herein, the terms "RNA export element" or "Pre-mRNA Processing Enhancer (PPE)" refer to 3' and 5' cis-acting post-transcriptional regulatory elements that enhance export of RNA from the nucleus. "PPE" elements include, but are not limited to Mertz sequences (described in U.S. Pat. Nos. 5,914,267 and 5,686,120, all of which are incorporated herein by reference) and woodchuck mRNA processing enhancer (WPRE; WO99/14310, incorporated herein by reference).

As used herein, the term "polycistronic" refers to an mRNA encoding more than polypeptide chain (See, e.g., WO 93/03143, WO 88/05486, and European Pat. No. 117058, all of which is incorporated herein by reference). Likewise, the term "arranged in polycistronic sequence" refers to the arrangement of genes encoding two different polypeptide chains in a single mRNA.

As used herein, the term "internal ribosome entry site" or "IRES" refers to a sequence located between polycistronic genes that permits the production of the expression product originating from the second gene by internal initiation of the translation of the dicistronic mRNA. Examples of internal ribosome entry sites include, but are not limited to, those derived from foot and mouth disease virus (FDV), encephalomyocarditis virus, poliovirus and RDV (Scheper et al., Biochem. 76: 801–809 [1994]; Meyer et al., J. Virol. 69: 2819–2824 [1995]; Jang et al., 1988, J. Virol. 62: 2636–2643 [1998]; Haller et al., J. Virol. 66: 5075–5086 [1995]). Vectors incorporating IRES's may be assembled as is known in the art. For example, a retroviral vector containing a polycistronic sequence may contain the following elements in operable association: nucleotide polylinker, gene of interest, an internal ribosome entry site and a mammalian selectable marker or another gene of interest. The polycistronic cassette is situated within the retroviral vector between the 5' LTR and the 3' LTR at a position such that transcription from the 5' LTR promoter transcribes the polycistronic message cassette. The transcription of the polycistronic message cassette may also be driven by an internal promoter (e.g., cytomegalovirus promoter) or an inducible promoter, which may be preferable depending on the use. The polycistronic message cassette can further comprise a cDNA or genomic DNA (gDNA) sequence operatively associated within the polylinker. Any mammalian selectable marker can be utilized as the polycistronic message cassette mammalian selectable marker. Such mammalian selectable markers are well known to those of skill in the art and can include, but are not limited to, kanamycin/G418, hygromycin B or mycophenolic acid resistance markers.

As used herein, the term "retrovirus" refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell.

As used herein, the term "retroviral vector" refers to a retrovirus that has been modified to express a gene of interest. Retroviral vectors can be used to transfer genes efficiently into host cells by exploiting the viral infectious process. Foreign or heterologous genes cloned (i.e., inserted using molecular biological techniques) into the retroviral genome can be delivered efficiently to host cells which are susceptible to infection by the retrovirus. Through well known genetic manipulations, the replicative capacity of the retroviral genome can be destroyed. The resulting replication-defective vectors can be used to introduce new genetic material to a cell but they are unable to replicate. A helper virus or packaging cell line can be used to permit vector particle assembly and egress from the cell. Such retroviral vectors comprise a replication-deficient retroviral genome containing a nucleic acid sequence encoding at least one gene of interest (i.e., a polycistronic nucleic acid sequence can encode more than one gene of interest), a 5' retroviral long terminal repeat (5' LTR); and a 3' retroviral long terminal repeat (3' LTR).

The term "pseudotyped retroviral vector" refers to a retroviral vector containing a heterologous membrane protein. The term "membrane-associated protein" refers to a protein (e.g., a viral envelope glycoprotein or the G proteins of viruses in the Rhabdoviridae family such as VSV, Piry, Chandipura and Mokola) which are associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the Rhabdoviridae family.

The term "heterologous membrane-associated protein" refers to a membrane-associated protein which is derived from a virus which is not a member of the same viral class or family as that from which the nucleocapsid protein of the vector particle is derived. "Viral class or family" refers to the taxonomic rank of class or family, as assigned by the International Committee on Taxonomy of Viruses.

The term "Rhabdoviridae" refers to a family of enveloped RNA viruses that infect animals, including humans, and plants. The Rhabdoviridae family encompasses the genus Vesiculovirus which includes vesicular stomatitis virus (VSV), Cocal virus, Piry virus, Chandipura virus, and Spring viremia of carp virus (sequences encoding the Spring viremia of carp virus are available under GenBank accession number U18101). The G proteins of viruses in the Vesiculovirus genera are virally-encoded integral membrane proteins that form externally projecting homotrimeric spike glycoproteins complexes that are required for receptor binding and membrane fusion. The G proteins of viruses in the Vesiculoviruses genera have a covalently bound palmititic acid ($C_{16}$) moiety. The amino acid sequences of the G proteins from the Vesiculoviruses are fairly well conserved. For example, the Piry virus G protein share about 38% identity and about 55% similarity with the VSV G proteins (several strains of VSV are known, e.g., Indiana, New Jersey, Orsay, San Juan, etc., and their G proteins are highly homologous). The Chandipura virus G protein and the VSV G proteins share about 37% identity and 52% similarity. Given the high degree of conservation (amino acid sequence) and the related functional characteristics (e.g., binding of the virus to the host cell and fusion of membranes, including syncytia formation) of the G proteins of the Vesiculoviruses, the G proteins from non-VSV Vesiculoviruses may be used in place of the VSV G protein for the pseudotyping of viral particles. The G proteins of the Lyssa viruses (another genera within the Rhabdoviridae family) also share a fair degree of conservation with the VSV G proteins and function in a similar manner (e.g., mediate fusion of membranes) and therefore may be used in place of the VSV G protein for the pseudotyping of viral particles. The Lyssa viruses include the Mokola virus and the Rabies viruses (several strains of Rabies virus are known and their G proteins have been cloned and sequenced). The Mokola virus G protein shares stretches of homology (particularly over the extracellular and transmembrane domains) with the VSV G proteins which show about 31% identity and 48% similarity with the VSV G proteins. Preferred G proteins share at least 25% identity, preferably at least 30% identity and most preferably at least 35% identity with the VSV G proteins. The VSV G protein from which New Jersey strain (the sequence of this G protein is provided in GenBank accession numbers M27165 and M21557) is employed as the reference VSV G protein.

As used herein the term, the term “in vitro” refers to an artificial environment and to processes or reactions that occur within an artificial environment. In vitro environments can consist of, but are not limited to, test tubes and cell cultures. The term “in vivo” refers to the natural environment (e.g., an animal or a cell) and to processes or reaction that occur within a natural environment.

As used herein, the term “purified” refers to molecules, either nucleic or amino acid sequences, that are removed from their natural environment, isolated or separated. An “isolated nucleic acid sequence” is therefore a purified nucleic acid sequence. “Substantially purified” molecules are at least 60% free, preferably at least 75% free, and more preferably at least 90% free from other components with which they are naturally associated.

DETAILED DESCRIPTION OF THE INVENTION

The present invention relates to transgenic animals that express exogenous growth factors in their milk, and in particular to pigs that express exogenous growth factors in their milk. In some embodiments, the growth factor is selected from the group including, but not limited to, IGF-I (insulin-like growth factor I), IGF-II (insulin like growth factor II), EGF (epidermal growth factor), PDGF (platelet derived growth factor), FGF (fibroblast growth factor), and TGF (transforming growth factor). In some embodiments, the gene is human IGF-I (e.g., SEQ ID NO:2). In other embodiments, the nucleic acid encoding the IGF-1 gene hybridizes to SEQ ID NO:2 under conditions of low to high stringency. In preferred embodiments, the growth factor gene is part of a gene construct (e.g., SEQ ID NO:1). In some preferred embodiments, the gene construct further comprises a mammary-specific promoter/enhancer region (e.g., including but not limited to those derived from the casein, whey acidic, lactoferrin, and lactoglobin promoters and variants and homologs thereof).

In some embodiments, the present invention provides transgenic pigs that produce a growth factor (e.g., IGF-I) in their milk. In preferred embodiments, piglets suckling milk from transgenic pigs have an increased rate of growth compared to piglets suckling from non-transgenic pigs. Additionally, in preferred embodiments, piglets suckling from transgenic pigs have increased levels of intestinal lactase and improved intestinal health.

I. Growth Factors

A. Growth Factor Genes

In some embodiments, the present invention provides transgenic animals (e.g., pigs) that expresses exogenous growth factors (e.g., IGF-I, IGF-II, and EGF and homologs thereof) in their milk. IGF-I is highly conserved, with the human, porcine, ovine and bovine sequences showing 100% homology at the amino acid level (Tavakkol et al., Molec Endocrinol., 2:674 [1988]).

IGF-I and IGF-II are approximately 7.5 kDa peptides which exhibit 70% amino acid homology with each other and 50% homology with proinsulin.

IGF-I and IGF-II are products of two distinct genes. IGF-I and IGF-II interact with specific receptors, the type I and type II IGF receptors, respectively, but also cross react to some degree with each other’s receptors. Both interact with binding proteins, but there are differences in the affinity of different binding proteins for IGF-I vs. IGF-II. IGF-I and IGF-II participate in many of the same physiological actions, but have discrete actions of their own as well.

In some embodiments, the methods and compositions of the present invention utilize the human IGF-I gene (e.g., SEQ ID NO:2). In other embodiments, the methods and compositions of the present invention utilize another growth factor (e.g., a different IGF-I gene, an IGF-IL gene, or an EGF gene), including but not limited to those described in Table 1 below.

TABLE 1

Growth Factor Genes

| Organism | Gene | Accession Number(s) |
|---|---|---|
| Human | IGF-I | E01712; E01709; E01168; E00602; E00306; E00305; E00304; E00303; S85346; X03422; X03421; X03420; X03419; X57025; X03563; U40870; M59812; M37484; M37483; M27544; AH002705; M14156; M14155; M14154; M14153; M12659; |
| Pig | IGF-I | X64400 |
| Mouse | IGF-I | AF056187; X04480; M28139 |
| Rat | IGF-I | D00698; AA926152; S68686; S68264; S43941; X06108; X06107; M15481; M17335; M15480; M27293; AH002176 |
| Japanese Quail | IGF-I | AF260131; S75247 |
| Goat | IGF-I | SEG_GOTIGFI; D26118; D26116; D26119; D26117; D11378 |
| Ostrich | IGF-I | AB035804 |
| Japanese Flounder | IGF-I | AJ010602; AJ010603 |
| Musk Shrew | IGF-I | D43957 |
| Goldfish | IGF-I | AF001006; AF001005 |
| Black Seabream | IGF-I | AF030573 |
| Scorpion fish | IGF-I | Y12583 |
| Turkey | IGF-I | AF074980 |
| chum Salmon | IGF-I | AF063216; AH004580; S70778; S70777 |
| Mozambique Tilapia | IGF-I | AH006116; AF033800; AF033799; AF033798; AF33797; AF033796 |
| Rabbit | IGF-I | U75390 |
| Sheep | IGF-I | X51403; X51358; X51357; M31734; M30653;M31735;M31736 |

TABLE 1-continued

Growth Factor Genes

| Organism | Gene | Accession Number(s) |
|---|---|---|
| Catfish | IGF-I | X79077; X79244; |
| Guinea Pig | IGF-I | X52951 |
| Xenopus | IGF-I | M29857 |
| Chinook Salmon | IGF-I | U15962; U15961; U15960; U14536 |
| Coho Salmon | IGF-I | M32792 |
| Chicken | IGF-I | M32791 |
| Bovine | IGF-II | E01192;X53867 |
| Sheep | IGF-II | Y16533; U00668; U00667; U00666; U00665; U00664; U00663; M89789; M89788 |
| Human | IGF-II | X03427; X07868; S77035; X03426; X03425; X03424; X03562; X05330; X05331; X07867; X03423; A18005; A18004; AH002704; M22373; M22372; AH002703; M14118; M14117; M14116; M13970; M17862 |
| Mouse | IGF-II | BE335824; AW822068; AW743221; AW742693; AW742516; AW742405; NM_010514; AI562175; AI325269; AI157816; U71085; AI120019; AA409837; AA407349; C80191; AA958906; AA959114; X71922; X71921; X71920; X71919; X71918; M36334; M36333; AH001929; M36332; M36331; M36330; M36329 |
| Mozambique Tilapia | IGF-II | AH006117; AF033804; AF033803; AF033802; AF033801 |
| Zebra Finch | IGF-II | AJ223165 |
| Rat | IGF-II | AH005814; M13871; M13870; M13869; M13868; M22474; AH002187; M29880; M29879; M29878; M17960 |
| Chum Salmon | IGF-II | X9725 |
| Barramundi Perch | IGF-II | AF007943 |
| Chicken | IGF-II | AH005039; S82962 |
| Bovine | EGF | L12259 |
| Pig | EGF | AF079769; AF079768 |
| Mouse | EGF | NM019397; NM_010113; X74038; J00380 |
| Rat | EGF | NM_012842 |
| Human | EGF | NM_005928; NM_001963; E02238; E01114; E00779; E00309; E00208; L17030; L17029 |
| Sheep | EGF | X89506 |
| Chicken | EGF | Y09264 |
| Human | PDGF | AF244813; NM_002608; AF169595; AH007345; S50869; 261626; S51624; E02395; X02811; X03795; X06374 |
| Mouse | PDGF | NM_008808; AF286725; AH004413 |
| Chicken | FGF | AB030229; U55189 |
| Bovine | FGF | AJ003123; M13440; M13439 |
| Sheep | FGF | AF213396 |
| Human | FGF | NM_019851; AB021975; AB030648; AB044277; NM_019113 |
| Rat | FGF | NM_019199; NM_019198 |
| Mouse | FGF | AB025718; AB029498; NM_010202; NM_010201 |
| Bovine | TGF | M36271 |
| Porcine | TGF | X14150; X12373; X70142 |
| Mouse | TGF | NM_019678; NM_009368 |
| Human | TGF | NM_003239; X05844; NM_009368 |

B. Biological Activity of Growth Factors

In some embodiments, the present invention provides animals (e.g., pigs) that express a growth factor gene in their milk during lactation. In some embodiments, the transgenic animal is a female. In other embodiments, the transgenic animal is a lactating male animal. Methods are known in the art for inducing lactation in animals. For example, lactation can be induced in bovines by repeated injections of estradiol and progesterone (See e.g., Smith and Schanbacher, J. Dairy Sci., 56:758 [1973]; and Sawyer et al., J. Dairy Sci., 69:1536 [1986]). It is contemplated that offspring (e.g., piglets) that suckle transgenic animals expressing growth factors in their milk will have improved intestinal health and development.

1. Effect of Growth Factors on Mammary Growth and Nutrient Uptake

The present invention is not limited to any one mechanism. Indeed, an understanding of the mechanism is not necessary to practice the present invention. Nonetheless, IGF-I is thought to mediate a portion of the effects of growth hormone on lactation (Cohick, J. Dairy Sci., 81:1769 [1998]). It is contemplated that IGF-I has an effect in regulating mammary growth and differentiation. IGF-I has been shown to stimulate cellular growth and DNA synthesis in cultured bovine and ovine mammary tissues (Shamay et al., Endocrinology, 123:804 [1988]; Wunder et al., J. Endocrinology, 123:319 [1989]). IGF-I has also been shown to have mitogenic activity and to be an inhibitor of mammary apoptosis (Cohick, J. Dairy Sci., 81:1769 [1998]; Neuenschwander et al., J. Clin Invest., 97:2225 [1996]; Rosfjord and Dickson, J. Mamm. Gland Biol. Neoplasia, 4:229 [1999]).

Mammary and intestinal tissue share several key nutrient uptake systems. Several of these transporters utilize an electrochemical gradient of $Na^+$ (Shennan, J. Mam. Gland Biol. Neoplasia, 3:247 [1998]). For example, glucose uptake by the mammary gland occurs by both the GLUT and SGLT systems. Glucose uptake across the GLUT transporter occurs by facilitative diffusion, whereas the SGLT transporter utilizes the $NA^+$ Gradient (Shennan, J. Mam. Gland Biol. Neoplasia, 3:247 [1998]). Sodium-dependent glucose uptake in pig intestine is increased by IGF-I (Alexander and Carey, Am. J. Physiol., 277: G619 [1999]). The present invention is not limited to any one mechanism. Indeed, an understanding of the mechanism is not necessary to practice the present invention. Nonetheless, it is contemplated that expression of a growth factor (e.g., IGF-I) in the mammary gland of an animal (e.g., a pig) modulates nutrient transport within mammary epithelial tissue. Specifically, it is contemplated that the overexpression of a growth factor (e.g., IGF-I) in the mammary gland will enhance early mammary development and mammary function in lactation, and will inhibit involution.

Example 5 describes experiments investigating the effect of one growth factor (IGF-I) on mammary gland development and nutrient uptake. It is contemplated that the mammary glands of sows overexpressing IGF-I will show enhanced proliferation and reduced apoptosis compared to control non-transgenic siblings. For example, it is contemplated that the overexpression of IGF-I in the mammary glands of sows will decrease involution of the mammary glands, resulting in longer lactation and increased milk production. Additionally, it is contemplated that these alterations in cellular proliferation and cell death will lead to an increase in mammary cellularity and changes in mammary morphology. Furthermore, it is contemplated that $Na^+$ coupled nutrient transport as well as kinetic properties of valine and glucose uptake will be enhanced in tissue from transgenic, but not control sows.

2. Effect of Exogenous Growth Factors on Sow Milk

In some embodiments, the present invention provides methods of increasing piglet growth and intestinal lactase activity. Example 3 describes the measurement of several properties of milk from transgenic sows overexpressing IGF-I compared to non-transgenic control sows. Properties investigated include total milk production, IGF-I and IGF-I binding protein levels in milk, total milk solids, milk protein content, and milk fat content.

Figure 4:
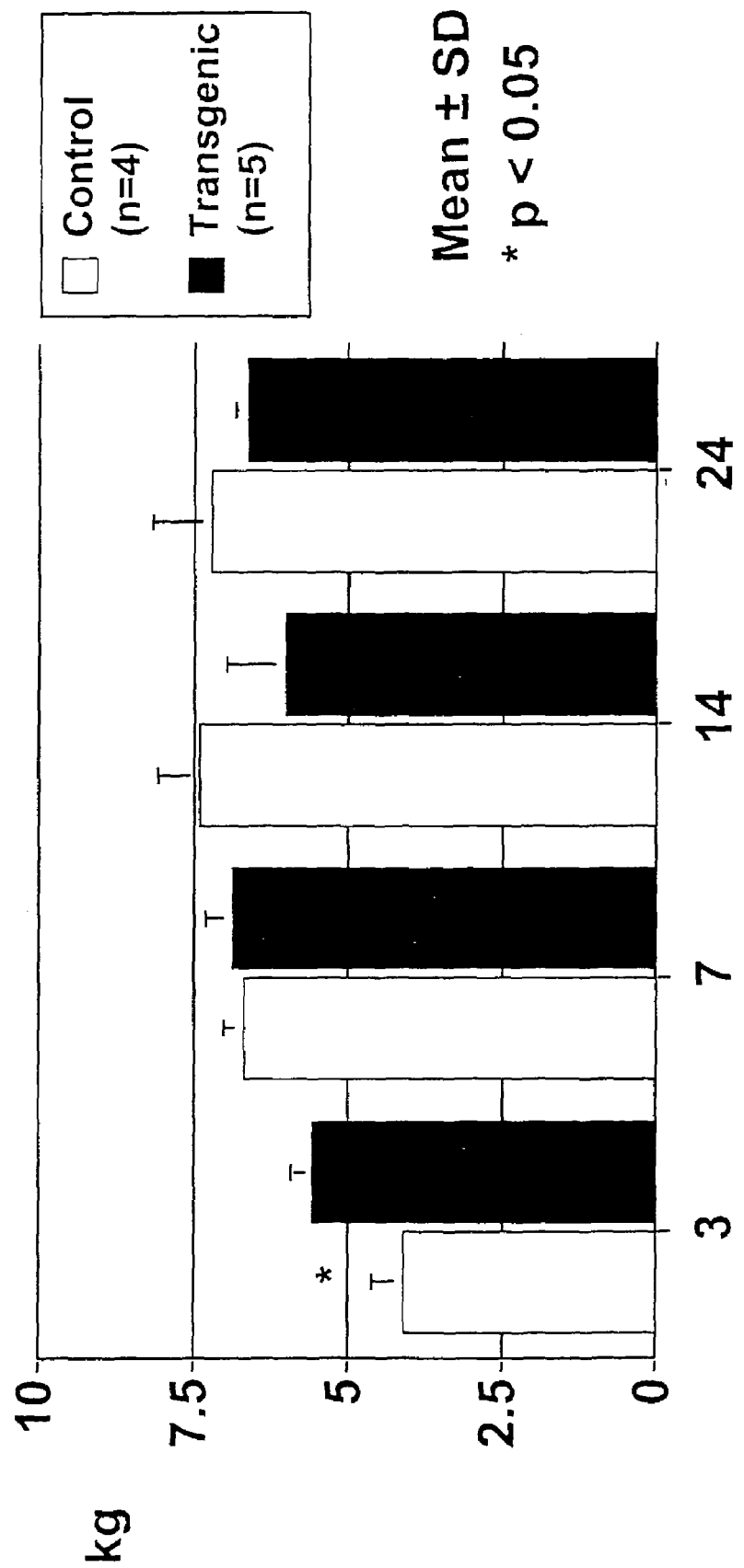
FIG. 4 shows milk production of transgenic sows expressing IGF-I and non-transgenic control sows.
Figure 5:
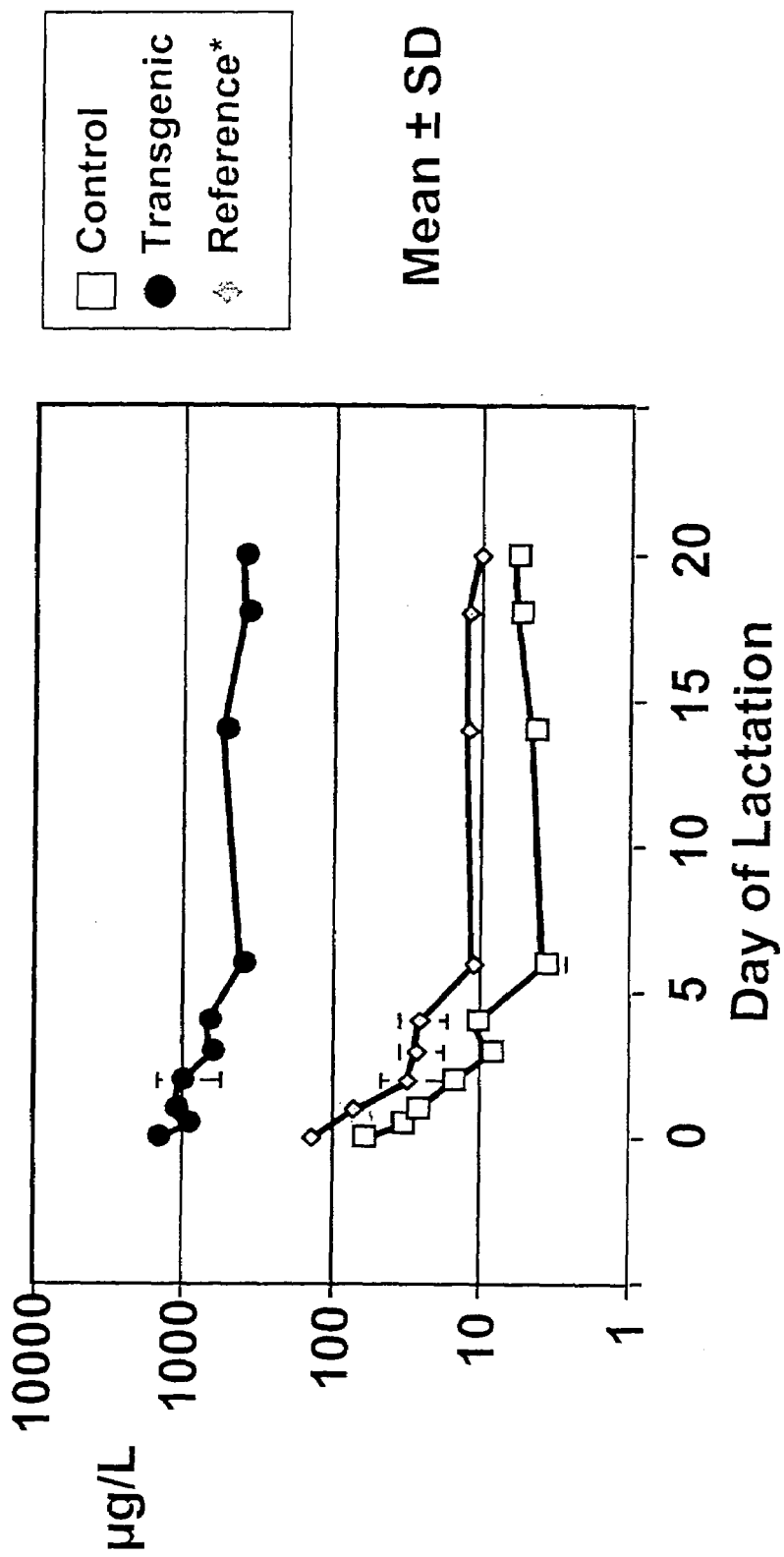
FIG. 5 shows IGF-I content in the milk of transgenic sows expressing IGF-I and non-transgenic control sows.
Figure 6:
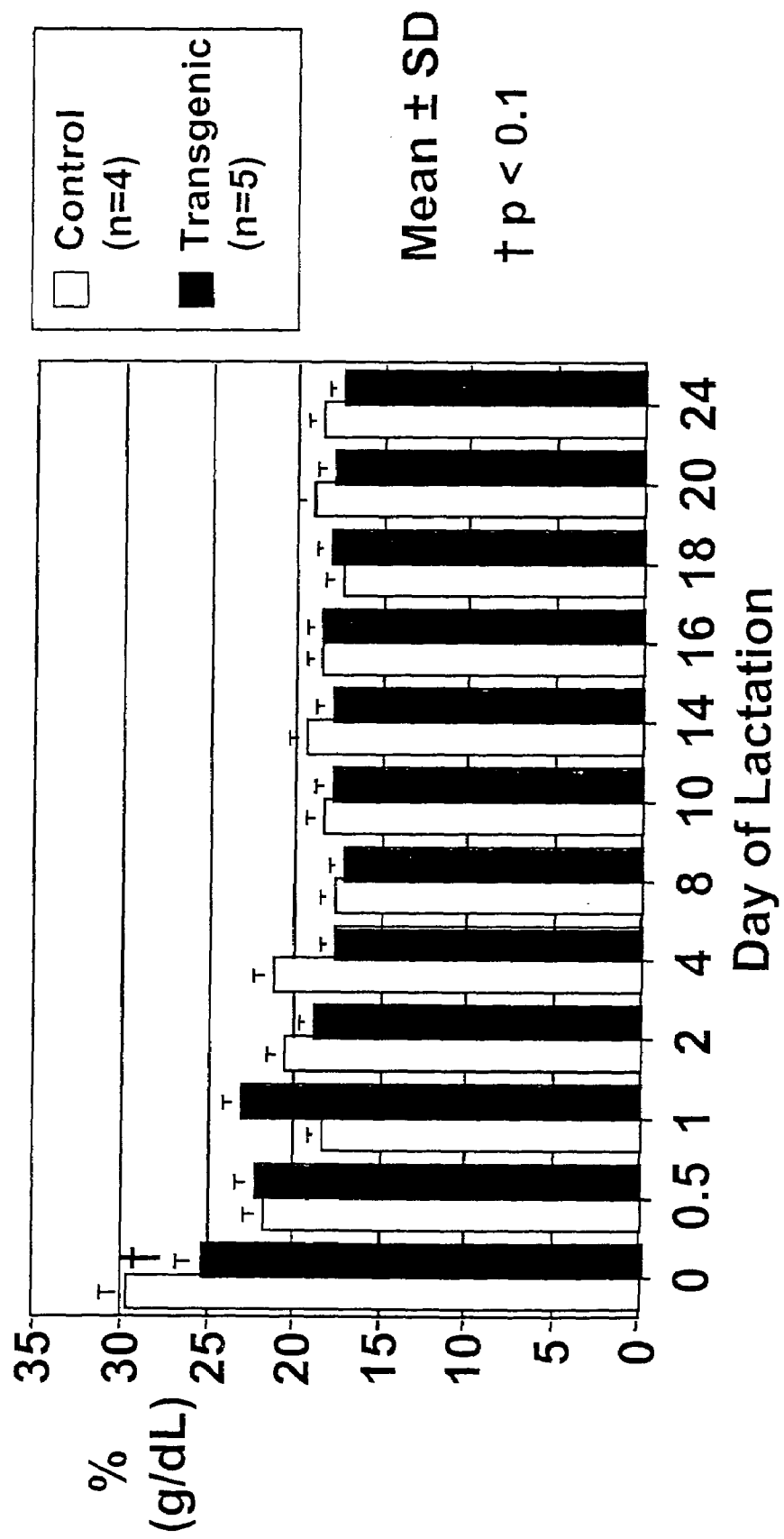
FIG. 6 shows the level of milk solids in the milk of transgenic sows expressing IGF-I and non-transgenic control sows.
Figure 7:
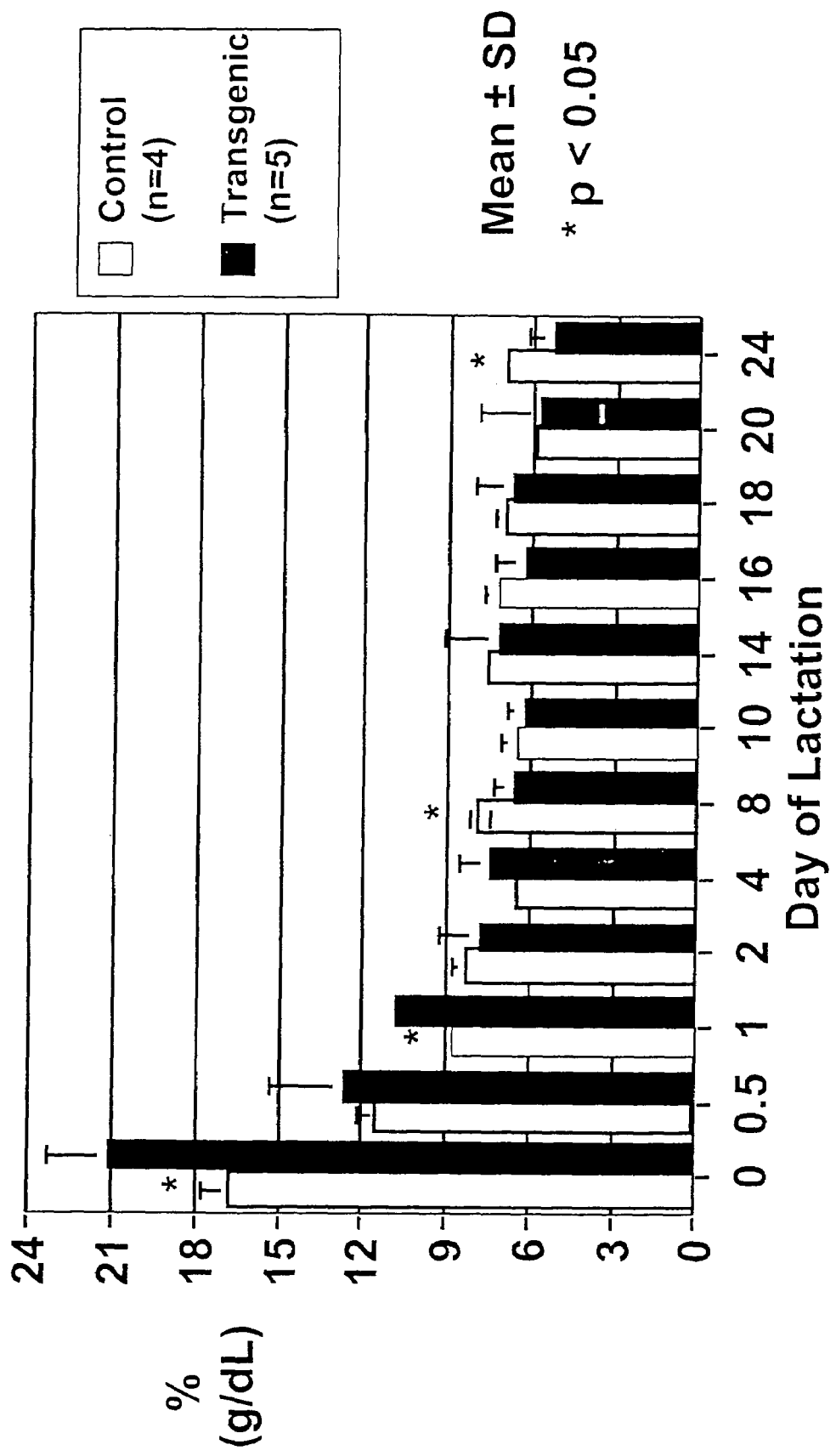
FIG. 7 shows protein content in the milk of transgenic sows expressing IGF-I and non-transgenic control sows.
Figure 8:
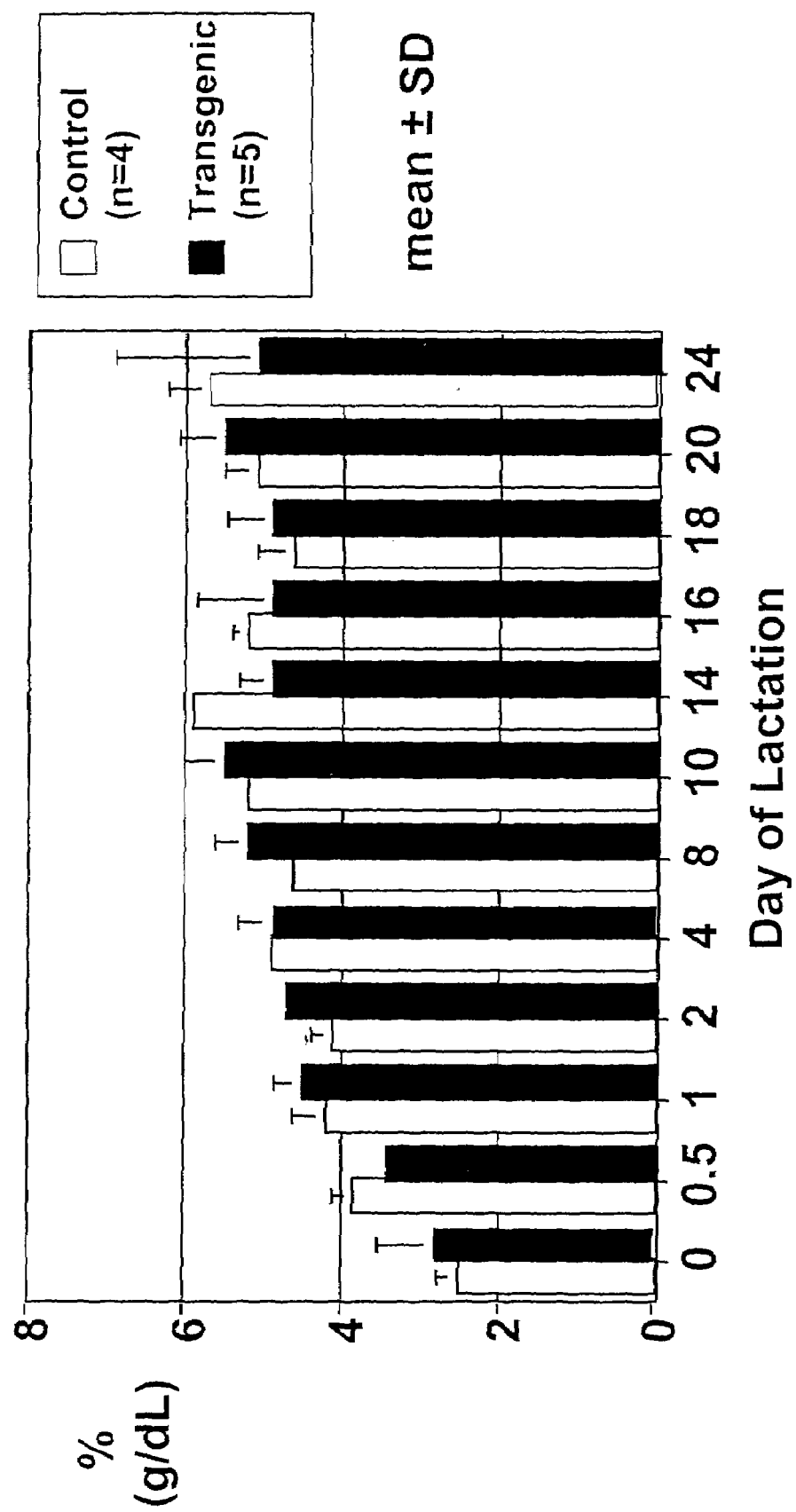
FIG. 8 shows the lactose content in the milk of transgenic sows expressing IGF-I and non-transgenic control sows.
Figure 9:
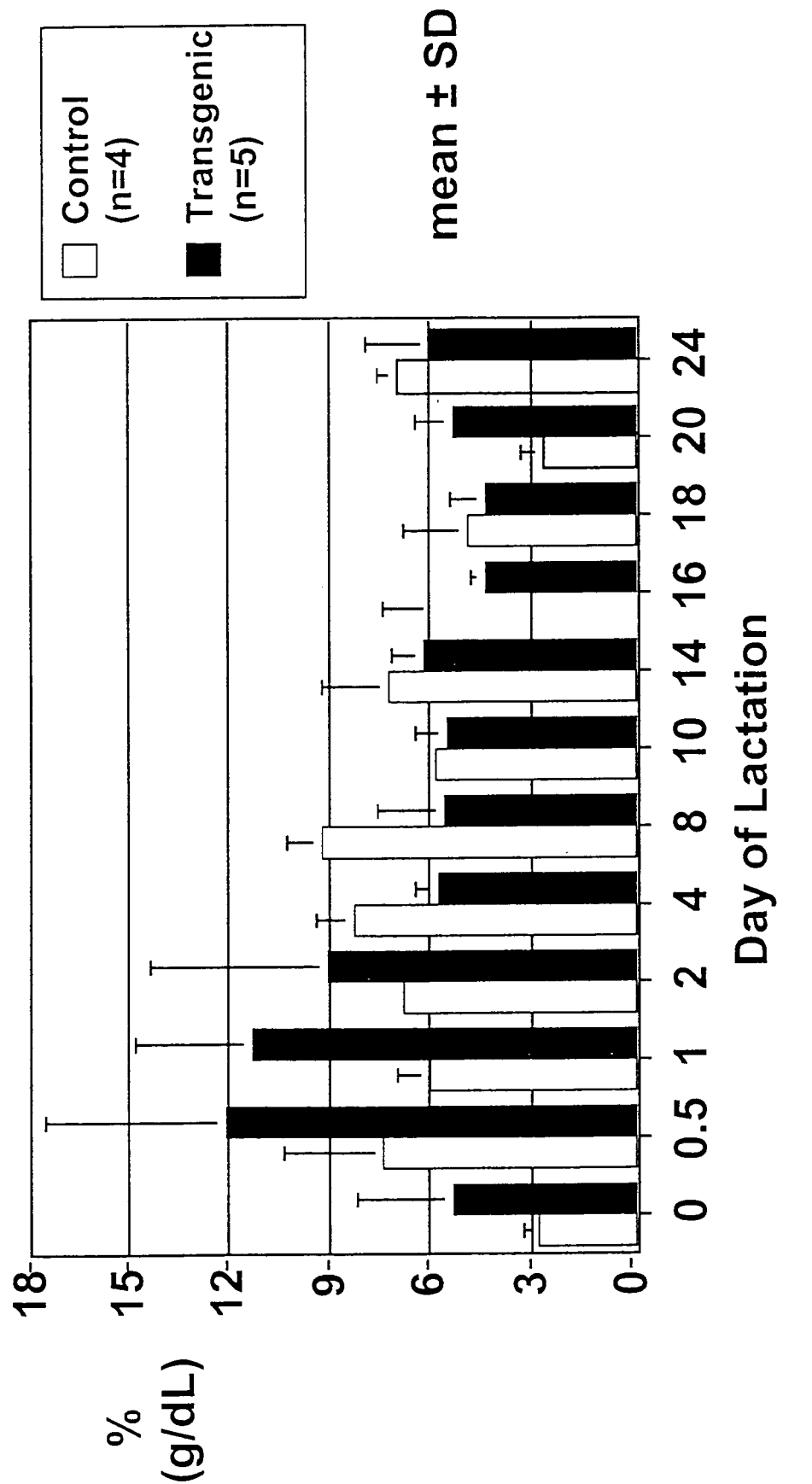
FIG. 9 shows the fat content in the milk of transgenic sows expressing IGF-I and non-transgenic control sows.

Milk production was found to be higher in transgenic sows relative to control sows on day 3 of lactation (Example 3A; FIG. 4). The IGF-I content of colostrum of transgenic sows was found to approximately 10 fold higher than non-transgenic control sows (Example 3B; FIG. 5). The increased IGF-I content was maintained throughout lactation. The milk of transgenic sows was found to contain increased levels of IGFBP5 relative to non-transgenic control animals (Example 3C). Protein levels were higher in the milk of transgenic sows on days 0, and 1 of lactation and were higher in control samples on days 8 and 24 of lactation (Example 3E; FIG. 7). Milk from transgenic sows had a higher fat content at days 0–2 of lactation (Example 3G; FIG. 9). The level of milk solids was lower in transgenic sows than control sows at day 0 of lactation (Example 3D; FIG. 6). Levels of milk solids were similar in transgenic and control samples for the remainder of the study. The lactose content of milk samples from transgenic and non-transgenic sows was not found to be significantly different (Example 3F; FIG. 8).

3. Effect of Growth Factors on Neonatal Intestinal Development

The present invention is not limited to any one mechanism. Indeed, an understanding of the mechanism is not necessary to practice the present invention. Nonetheless, it is contemplated that the expression of a growth factor (e.g., IGF-I) in the milk of transgenic sows will have a beneficial effect on intestinal development and health of suckling piglets. Specifically, it is contemplated that piglets suckling from sows expressing a growth factor (e.g., IGF-I) will have increased resistance to intestinal disease, increased nutrient metabolism, and increased hardiness during weaning.

Figure 2:
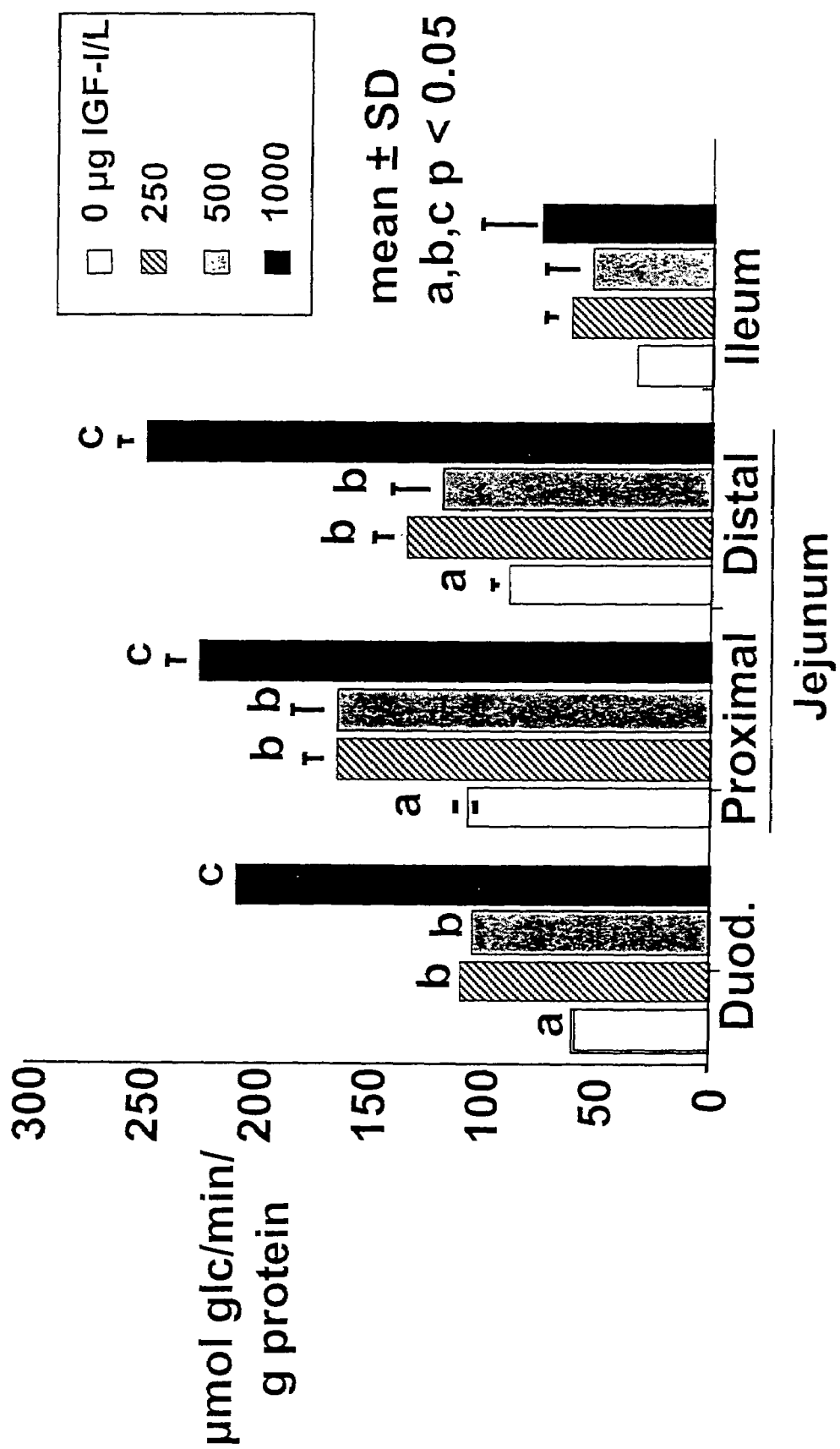
FIG. 2 shows lactase activity in various segments of piglet intestine in response to varied levels of oral IGF-I.
Figure 11:
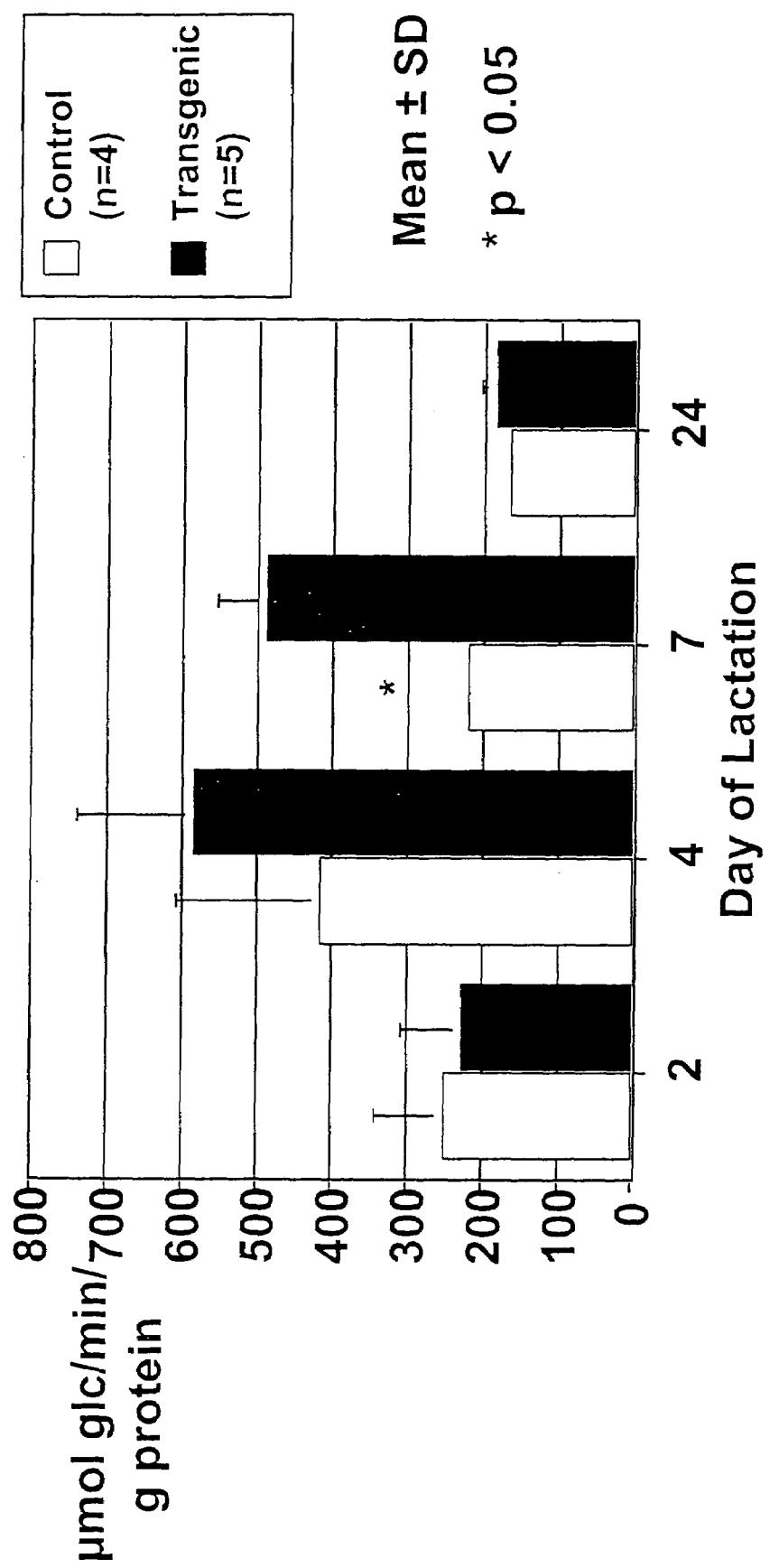
FIG. 11 shows lactase activity in the intestines of piglets suckling transgenic sows expressing IGF-I and non-transgenic control sows.

Oral administration of IGF-I was shown to increase intestinal lactase activity (Example 1; FIGS. 1 and 2). Piglets suckling transgenic sows expressing IGF-I in their milk were found to have increased intestinal lactase activity (Example 4B; FIG. 11).

Example 6 describes experiments designed to further investigate the effect of IGF-I on piglet intestinal morphology, disaccharidase gene expression, nutrient transport and ion secretion, nutrient transporter gene expression, and nutrient transporter protein abundance. It is contemplated that intestinal villus morphology and disaccharidase activity will be greater in piglets suckling transgenic sows. It is further contemplated that $Na^+$-coupled glucose and glutamine transport will be greater in the intestines of piglets suckling transgenic sows. In addition, it is contemplated that the maximum uptake rate of piglets suckling transgenic sows will be greater because of the enhanced efflux of intracellular $Na^+$. Additionally, it is contemplated that piglets suckling transgenic sows will have increased cell division in the small intestine. Finally, it is contemplated that increased $Na^+,K^+$-ATPase activity and protein levels will be observed.

It is contemplated that piglets suckling from transgenic sows expressing a growth factor (e.g., IGF-I) in their milk will have increased intestinal health and resistance to intestinal diseases. Specifically, it is contemplated that piglets will have increased resistance to scours. Scours is a common pathogenic intestinal disease of suckling piglets. Scouring may be caused by pathogens including, but not limited to rotovirus, coronavirus, *E. coli*, and *salmonella*.

II. Methods of Generating Transgenic Animals

A. Gene Constructs

In some embodiments, transgenic animals (e.g., pigs) are generated using the gene construct described in SEQ ID NO:1. In some embodiments, the gene construct contains the human IGF-I gene (SEQ ID NO:2). In other embodiments, the gene construct contains a growth factor gene, including, but not limited to those described in Table 1.

In some embodiments, the gene construct further comprises a promoter. In preferred embodiments, the promoter comprises a mammary preferential or specific promoter. In some embodiments, the mammary preferential or specific promoter is selected from the group including, but not limited to alpha-lactalbumin, casein promoters (e.g., alpha S1-, beta-, and kappa-), whey acidic promoter, and lactoferrin promoter (described in U.S. Pat. Nos. 6,004,805; 6,027,722; 5,304,489; 5,565,362; 5,831,141; 4,873,316; and European Patent No. 264,166; all of which are herein incorporated by reference). In some embodiments, the promoter comprises the bovine alpha-lactalbumin promoter. Some mammary specific promoters (e.g., lactoferrin) direct expression only lactation (See e.g., Goodman and Schanbacher, Biochem Biophys Res Commun., 180:75 [1991]).

In some embodiments of the present invention, the gene construct further comprises a signal peptide to signal secretion of the protein of interest. The sequences of several suitable signal peptides are known in the art, including, but not limited to, those derived from tissue plasminogen activator, human growth hormone, lactoferrin, alpha S1-casein, and alpha-lactalbumin.

B. Methods of Introducing DNA into the Genome of Animals

In some embodiments, the present invention provides a transgenic animal (e.g., a pig) expressing a growth factor (e.g., IGF-I) in their milk. The present invention is not limited to any one method of generating transgenic animals. In some embodiments, the transgenic animals are generated by pronuclear microinjection. In other embodiments, the transgenic animals are generated by nuclear transfer. In still further embodiments, the transgenic animals are generated by retroviral infection of oocytes or embryos.

1. Pronuclear Microinjection

In some embodiments, the transgenic animals of the present invention are generated by pronuclear microinjection (Bleck et al., J. Anim. Sci., 76:3072 [1998]; also described in U.S. Pat. Nos. 6,066,725, 5,523,226; 5,453,457; 4,873,191; 4,736,866, all of which are herein incorporated by reference). In pronuclear microinjection, several hundred copies of DNA are injected into the male pronuclear of the zygote. DNA integration occurs during replication as a repair function of the host DNA.

In some embodiments, pronuclear microinjection is performed on the zygote 12 hours post fertilization. Uptake of such genes may be delayed for several cell cycles. The consequence of this is that depending on the cell cycle of uptake, only some cell lineages may carry the transgene, resulting in mosaic offspring. If desired, mosaic animals can be bred to form true germline transgenic animals.

In one illustrative example of the present invention (Example 2), transgenic pigs were generated by pronuclear injection of the gene construct described in SEQ ID NO:1. In this example, 400 embryos were injected with the gene construct. Of 71 live births (from 14 pregnancies), 4 transgenic animals were identified, for a 5.6% efficiency of transgenic animals generated.

2. Nuclear Transfer

Nuclear transfer, dubbed "cloning" (described in U.S. Pat. Nos. 6,011,197; 5,496,720, 4,994,384; and 5,057,420, and WO 97/07669, WO 97/07668, and WO 95/17500; all of which are herein incorporated by reference), utilizes a nucleus extracted from non-germline cells to replace the nucleus of an oocyte from a donor animal. Nuclear transfer can be used as a means of gene introduction. In this case, a cell line is used as the starting point for gene introduction and then nuclei from this line are transferred into embryos for propagation. Genes can be introduced to the cell line using any suitable method (e.g., electroporation, transfection or injection)

3. Retroviral Infection

In some embodiments, the transgenic animals of the present invention are generated by retroviral gene transfer (Chan et al., PNAS, 95:14028 [1998]) and U.S. Pat. No. 6,080,912; herein incorporated by reference). In this method, an exogenous nucleic acid (e.g., IGF-I) is introduced into pre-maturation oocytes, mature unfertilized oocytes, or zygotes using retroviral vectors. In preferred embodiments, unfertilized oocytes are infected, permitting the integration of the recombinant provirus prior to the division of the one cell embryo. Thus, all cells in the embryo will contain the proviral sequences.

Retroviruses are enveloped (i.e., surrounded by a host cell-derived lipid bilayer membrane) single-stranded RNA viruses that infect animal cells. When a retrovirus infects a cell, its RNA genome is converted into a double-stranded linear DNA form (i.e., it is reverse transcribed). The DNA form of the virus is then integrated into the host cell genome as a provirus.

In preferred embodiments, pseudotyped retroviral vectors which contain the G protein of VSV as the membrane associated protein are used for the production of transgenic animals. Unlike retroviral envelope proteins which bind to a specific cell surface protein receptor to gain entry into a cell, the VSV G protein interacts with a phospholipid component of the plasma membrane (Mastromarino et al., J. Gen. Virol. 68:2359 [1987]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Bums et al., Proc. Natl. Acad. Sci. USA 90:8033 [1993]).

In some embodiments, the retroviral vectors are packaged and microinjected into the perivitelline space of oocytes (e.g., in vitro or in vivo matured oocytes). The oocytes are then fertilized. In other embodiments, zygotes are injected with the packaged retroviral vectors. The resulting embryos or zygotes can then be transferred into recipient animals.

Experimental

The following examples serve to illustrate certain preferred embodiments and aspects of the present invention and are not to be construed as limiting the scope thereof.

In the experimental disclosure which follows, the following abbreviations apply: M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml (milliliters); μl (microliters); cm (centimeters); mm (millimeters); μm (micrometers); nm (nanometers); ° C. (degrees Centigrade); AMP (adenosine 5'-monophosphate); BSA (bovine serum albumin); cDNA (copy or complimentary DNA); CS (calf serum); DNA (deoxyribonucleic acid); ssDNA (single stranded DNA); dsDNA (double stranded DNA); dNTP (deoxyribonucleotide triphosphate); KB (kilobase); bp (base pair); LH (luteinizing hormone); NIH (National Institutes of Health, Besthesda, Md.); RNA (ribonucleic acid); PBS (phosphate buffered saline); g (gravity); OD (optical density); HEPES (N-[2-Hydroxyethyl]piperazine-N-[2-ethanesulfonic acid]); HBS (HEPES buffered saline); PBS (phosphate buffered saline); SDS (sodium dodecylsulfate); Tris-HCl (tris[Hydroxymethyl]aminomethane-hydrochloride); Klenow (DNA polymerase I large (Klenow) fragment); EGTA (ethylene glycol-bis(β-aminoethyl ether) N,N, N',N'-tetraacetic acid); EDTA (ethylenediaminetetracetic acid); bla (β-lactamase or ampicillin-resistance gene); lacI (lac repressor); X-gal (5-bromo-4-chloro-3-indolyl-β-D-galactoside); ATCC (American Type Culture Collection, Rockville, Md.); GIBCO/BRL (GIBCO/BRL, Grand Island, N.Y.); Perkin-Elmer (Perkin-Elmer, Norwalk, Conn.); and Sigma (Sigma Chemical Company, St. Louis, Mo.); Intervet (Intervet, Millsboro, Del.); Packard (Packard Instruments, Meriden, Conn.); Micron Separation (Micron Separation, Inc., Westborough, Mass.); Pierce (Pierce, Rockford, Ill.); Novocastra (Novocastra Laboratories, Burlingham, Calif.); Fryer (Fryer Company, Inc., Carpentersville, Ill.); Universal Imaging (Universal Imaging Corp., Westchester, Pa.); Physiologic (Physiologic Instruments, Inc., San Diego, Calif.); Molecular Dynamics (Molecular Dynamics, Sunnyvale, Calif.); Oncogene Science (Oncogene Science Inc., Uniondale, N.Y.); Amersham (Amersham, Arlington Heights, Ill.).

EXAMPLE 1

Effect of Oral IGF-I on Piglet Development

Newborn, colostrum-deprived piglets were fed sow milk replacer alone or supplemented with 0, 0.25, 0.5, or 1.0 mg/L recombinant human IGF-I for 14 days. The effect of the oral IGF-I on lactase activity in piglet intestines was measured. The results are shown in FIGS. 1 and 2.

FIG. 1 shows lactase activity in various segments of the intestine in control piglets and piglets fed 1.0 mg/L IGF-I for 14 days. Segment 1 represents lactase levels in the duodenum; segments 2–7 represent the proximal jejunum; segments 8–11 represent the distal jejunum; and segments 12–13 represent the ileum. FIG. 2 shows lactase activity in various segments of the intestine in response to varied levels of oral IGF-I.

EXAMPLE 2

Generation of IGF-I Transgenic Pigs

A. α-LA/IGF-I Gene Construct

Pronuclear stage porcine embryos were injected with a α-LA/IGF-I gene construct (SEQ ID NO: 1; FIG. 3). The hybrid construct contains 210 bp of human IGF-I coding region (Exon 4) inserted in exon 1 of the bovine α-LAC gene. The construct also contains 2 kb of 5' flanking region from the bovine α-LAC gene, the bovine α-LAC signal peptide and promoter, Exons 2–4 of the bovine α-LAC gene including the polyA signal, and 329 bp of 3' flanking region.

This gene construct was created by inserting the cDNA encoding mature IGF-I behind the bovine α-lactalbumin signal peptide. Once this fusion was created it was then inserted into exon 1 of the bovine α-lactalbumin gene. The resulting mRNA produced from this gene construct resembles endogenous α-lactalbumin mRNA, except there is the additional IGF-I coding region contained within the exon 1 portion of the mRNA. The expression of this mRNA is under the control of the mammary specific bovine α-lactalbumin 5' flanking region.

The protein translated from this mRNA is a fusion of the bovine α-lactalbumin signal peptide and the human IGF-I mature protein. The signal peptide allows secretion of mature IGF-I into the milk after cleavage of the signal peptide in the rough endoplasmic reticulum.

B. Collection of Embryos

Embryos were collected and injected using previously described methods (Bleck et al., J. Anim. Sci., 76:3072 [1998]). Duroc, Yorkshire, and Duroc X Yorkshire gilts were injected with PG 600 (Intervet) at 170 to 210 days of age. Gilts that responded to the injection by exhibiting standing estrus continued in the study. These animal were injected with PMSG (Sigma) 16 days after standing estrus and then injected with hCG 72 hours later. Animal exhibiting standing estrus were artificially inseminated. Embryos were collected 54 hours after hCG injection by surgical embryo collection from the oviduct. 908 Embryos were flushed from the oviduct using Beltsville embryo culture medium (Dobrinsky et al., Biol. Reprod., 55:1069 [1996]). The embryos were centrifuged at 15,000×g for 5–10 minutes to visualize the pronuclei.

C. Injection and Transfer

Four hundred pronuclear embryos were injected with the α-LA/IGF-I gene construct. The injected DNA was at a concentration of approximately 4 ng/μl in microinjection buffer (10 mM Tris, 0.1 mM EDTA, pH 7.4). Approximately 20 normal-appearing injected embryos were transferred to each recipient animal. Recipient gilts were animals showing standing estrus within a day of the donor animal. Thirty six sows received embryos, resulting in 14 pregnancies and 71 live births.

The piglets were screened for the presence of the transgene using PCR. DNA was extracted from ear and tail and PCR was performed using the methods of Bleck and Bremel (J. Dairy Sci., 77:1897 [1994]). Transgenic pigs were characterized by the presence of a 360 bp product. Four of the piglets were transgenic, resulting in a 5.6% transgenic efficiency.

EXAMPLE 3

Properties of Milk of IGF-I Transgenic Sows

Transgenic gilts and control gilts were bred to the same non-transgenic boar and allowed to farrow. Litter sizes were adjusted to 10 piglets. Milk samples were obtained by manual expression on days 3, 7, 14, and 21 days post-lactation. Piglets were separated from the sow for one hour prior to milking. Sows were injected intravenously with 1.0 IU of oxytocin to promote milk let-down. Milk (50–100 ml) was collected into sterile containers and frozen immediately. Blood samples were collected from the ear vein for IGF-I and IGFBP studies.

A. Milk Production of Transgenic Sows

Milk yield was measured using the weigh-suckle-weigh technique (Lewis et al., J. Animal Sci., 47:634 [1978]). All of the piglets in a litter were removed from the sow for 1 hour, weighed, and returned to the sow and allowed to suckle for 15 minutes. Following suckling, the piglets were separated from the sow, weighed again, and kept separate from the sow until the next suckling period. The procedure was repeated every hour for 6 hours. The difference in body weight of the piglets before and after suckling was taken as the level of milk production.

FIG. 4 shows milk production of transgenic and control sows. Milk production was higher in transgenic sows relative to control sows on day 3 of lactation.

B. IGF-I Content in the Milk of Transgenic Sows

Milk samples were collected from transgenic, control, and reference (Donovan et al., Pediatric Res., 36:159 [1994]) sows between 12 hours and 20 days postpartum. Milk samples were de-fatted and casein was removed by acidification and centrifugation. Milk IGF-I was separated from IGFBP by chromatography in 0.2 mol/L formic acid (Donovan et al., 1994, supra). IGF-I fractions were collected and lyophilized. IGF recovery from the column was 90%. The concentration of IGF-I was measured using [$^{125}$I]-IGF-I as a competitive ligand and a polyclonal anti-human IGF-I antibody (NIH). After overnight incubation, 1% bovine IgG and 20% PEG (Sigma) was added and the tubes were centrifuged. Bound radioactivity was measured using a gamma counter (Cobra-II Autogamma counter, Packard). Concentrations were determined relative to a standard curve.

Data are shown in FIG. 5. IGF-I content was approximately 10 fold higher in the colostrum of transgenic sows than non-transgenic control sows. The increased IGF-I content in transgenic sows was maintained at approximately 60-fold higher in mature mild throughout lactation.

C. IGF-I Binding Protein Levels in Transgenic Sows

Serum and milk IGF binding protein (IGFBP) levels were measured by western ligand blotting (Donovan, 1994). Serum and milk whey samples (4 μl) were separated through 4% stacking and 12% running PAGE gels at 65V and 4° C. overnight. Proteins were electrotransferred to nitrocellulose (0.45 μm; Micron Separation) at 200 mA for 1 hour. Membranes were then sequentially blocked with TBS/3% tergitol NP-40, TBS/1% BSA (Sigma), and TBS/0/1% Tween. Membranes were incubated overnight with 1E10$^6$ cpm of [$^{125}$I]-IGF-I and IGF-I-BP was visualized by autoradiogroaphy. Radioactivity was quantitated using the Foto/analyst II Visionary System and Collage software.

The milk of transgenic sows was found to contain increased levels of IGFBP5 relative to non-transgenic control animals. No change in serum IGFBP was observed in transgenic sows relative to non-transgenic controls.

D. Level of Milk Solids in Transgenic Sows

Total milk solids in transgenic sows and non-transgenic controls was measured by scalding and drying 0.5 g of milk overnight in an oven at 1 00° C. The results are shown in FIG. 6. The level of milk solids was lower in transgenic sows than control sows at day 0 of lactation. Levels were similar in transgenic and control samples for the remainder of the study.

E. Protein Content in the Milk of Transgenic Sows

Protein concentration of milk samples was measured using the BCA assay (Pierce). Results are shown in FIG. 7. Protein levels were higher in the milk of transgenic sows on days 0, and 1 of lactation and were higher in control samples on days 8 and 24 of lactation.

F. Lactose Content in the Milk of Transgenic Sows

Lactose content of milk samples was measured using a colorimetric assay based on the method of Teles (J. Dairy Sci., 61:506 [1978]). The results are shown in FIG. 8. The lactose content of milk samples from transgenic and non-transgenic sows was not significantly different.

G. Fat Content in the Milk of Transgenic Sows

Fat content of milk samples was measured using a chloroform/methanol extraction method (Bligh and Dyer, Can. J. Biochem. Phys., 37:911 [1959]) that was been modified to a microassay requiring 0.5 ml of milk. The results are shown in FIG. 9. Milk from transgenic sows had a higher fat content than milk from non-transgenic control sows at days 0–2 of lactation.

Example 4

Effect of IGF-I Transgenic Milk on Suckling Piglets

A. Weight Gain of Suckling Piglets

Figure 10:
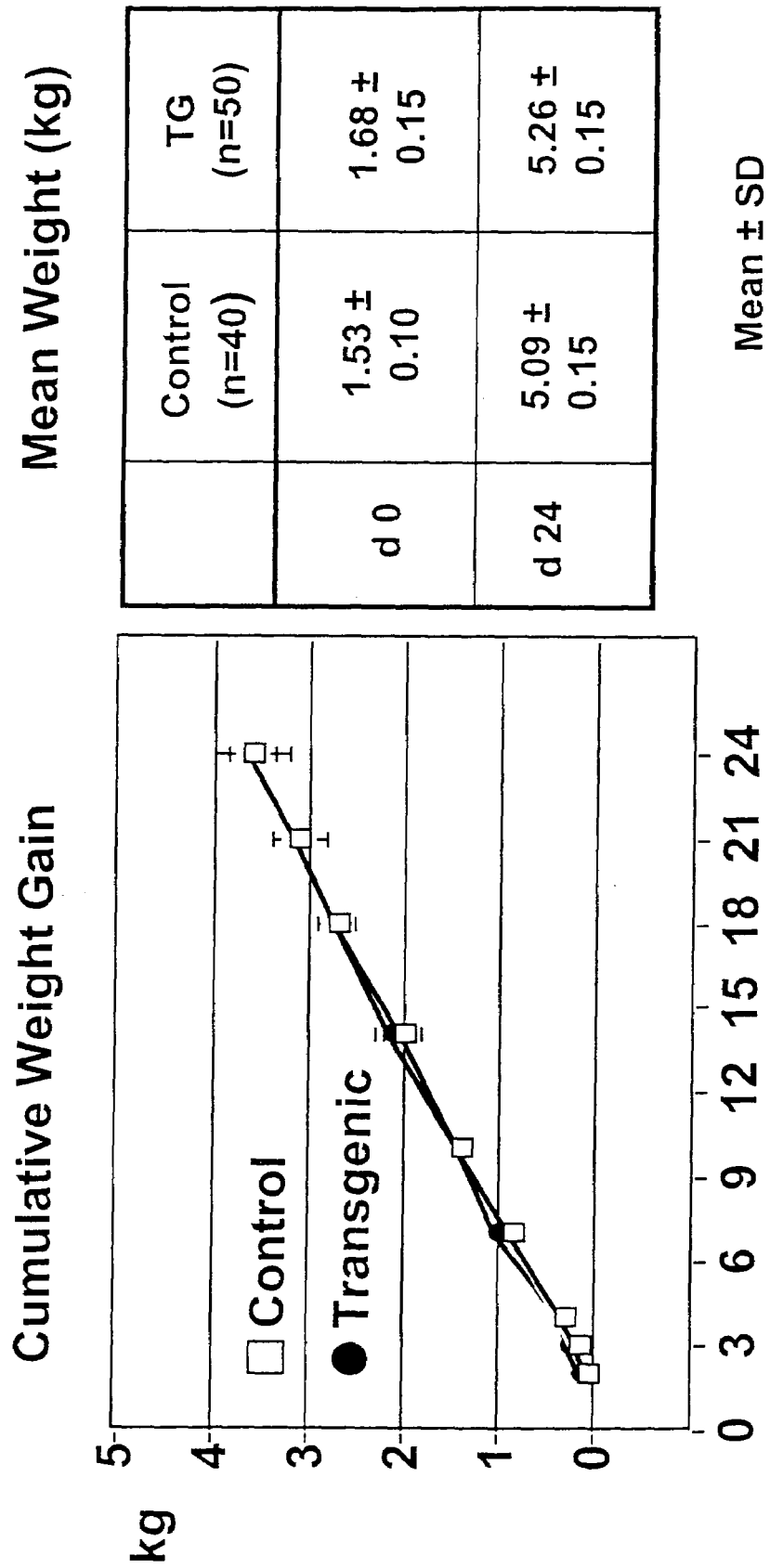
FIG. 10 shows weight gain of piglets suckling transgenic sows expressing IGF-I and non-transgenic control sows.

The weight of suckling piglets was obtained on days 3, 7, 14, and 21 days of lactation. FIG. 10 shows weight gain of piglets suckling transgenic and control sows. Piglets suckling transgenic sows showed a slightly increased cumulative weight gain during lactation. On day 24, the mean weight of piglets who nursed from transgenic sows was 5.26±0.15 kg (n=50) compared to 5.09±0.15 kg (n=40) in piglets who nursed from control sows.

B. Lactase Activity of Piglet Intestines

Piglets were killed by electrocution and exsanguination on the indicated days. The small intestine from the pyloric sphincter to the ileocecal valve was removed and separated from the mesentery. The weight and length of the entire intestine was determined and 50 cm samples representing jejunum (50% total length) and ileum (85% total length) were flushed with ice-cold 0.9% saline. Mucosal samples were collected by opening each segment longitudinally and scraping the luminal surface with a glass slide and then frozen in liquid nitrogen.

Lactase activity in intestinal samples was assayed using previously described methods (Houle et al., Pediatr. Res., 42:78 [1997]). Briefly, mucosal samples were homogenized in saline containing protease inhibitors (1 mM phenylmethysulfonylfluoride, 2 mM iodoacetic acid). Lactase activity was determined by incubating intestinal homogenates with lactose for 60 minutes at 37° C. Liberated glucose was assayed by glucose oxidase. Enzyme activity is expressed as umol glucose/minute/g protein.

Results are shown in FIG. 11. Lactase activity was higher in intestinal samples of piglets suckled on transgenic sows relative to control sows on days 4 and 7 of lactation.

EXAMPLE 5

Effect of Exogenous IGF-I on Mammary Growth

The effect of IGF-I overexpression on mammary growth, histomorphology, and nutrient uptake is measured in tissue samples from transgenic and control sows. Samples are collected at different stages of lactation and post-lactation.

Differences between the transgenic and non-transgenic controls will be determined using a repeated measures analysis of variance (Steele and Torrie (eds.), *Principles and Procedures of Statistics,* Second Edition, McGraw-Hill, New York, N.Y. [1980]). Computations are performed using the general linear model procedure in SAS (version 6.04; SAS Institute, Cary, N.C.; SAS, 1985).

A. Histomorphology

Formalin-fixed mammary tissue from sows at different days of lactation is embedded in paraffin, thin-sliced with a microtome, and stained with hematoxylin/eosin. Sections are histologically evaluated for lobular proliferation, secretory activity, and for changes in supporting stroma and adipose tissues (Neuenschwander et al., J. Clin. invest., 97:2225 [1996]). Sections showing involutional changes are evaluated for residual acinar proliferation and secretory change, extent of ducto-lobular luminal secretions, apoptosis of ductolobular epithelial and myoepithelial cells, and the nature and extent of the host inflammatory response. Apoptosis is identified histologically by the presence of prominent cytoplasmic eosinophilia, nuclear shrinkages and fragmentation and apoptotic bodies.

B. Apoptosis

The TUNEL assay is used to further localize cells exhibiting DNA fragmentation characteristic of apoptosis (Tanaka et al., 1996). In this assay, short fragments of DNA formed by endonucleases are detected with the use of terminal transferase enzyme (an enzyme that attaches deoxynucleotides to the 3' end of DNA fragments). Formalin-fixed mammary sections are used. Prepared slides are dipped in paraformaldehyde/PBS and then incubated in proteinase K for 15 minutes at 37° C. The slides are rinsed in TBS, pH 7.4 and sections are incubated in terminal transferase buffer (Boeringer Mannhein) containing biotinylated dUTP (Clonetech) in a humid atmosphere at 37° C. for 60 minutes. Endogenous peroxidase activity is inactivated by incubation in $H_2O_2$ for 20 minutes at room temperature. After washing and blocking with 10% goat serum, slides are incubated with streptavidin-conjugated peroxidase, washed with TBS, stained with deoxyaminobenzidine for several minutes and counterstained with methyl green. The number of apoptotic cells is counted by light microscopy. It is expected that mammary glands of sows overexpressing IGF-I will demonstrate decreased apoptosis as compared to controls non-transgenic sows.

C. Proliferation

Mammary cells undergoing proliferation will be detected immunohistochemically in mammary sections using a monoclonal antibody to cyclin A (Novocastra). Cyclin A is a 60 kDa protein which binds to cyclin-dependent kinase-2 in S to G2 phase of the cell cycle. Cyclin A is specific to cells undergoing DNA synthesis. Labelled cells are detected using streptavidin/biotin complex (Vectastain Elite, Novocastra). It is expected that mammary glands of sows overexpressing IGF-I will demonstrate increased proliferation as compared to controls non-transgenic sows.

D. Mammary Nutrient Uptake

Mammary amino acid uptake is assayed using well known techniques. For measurement of amino acid uptake, biopsy tissue is minced and washed three times in basal medium (5 mM KCL, 2 mM $CaCl_2$, 1 mM $MgSO_4$, 135 mM NaCl, 10 mM glucose, and 10 mM TRIS-BES, 7.4). For measurement of glucose uptake, concentrations of glucose are varied to determine kinetic properties of glucose transport (Alexander and Carey, [1999]). For determining sodium independence, NaCl in the basal medium is replaced with 135 mM choline chloride. Kinetic properties of the transport systems are determined by incubating explant tissue in the presence of a range of concentrations of lysine, valine, and glucose, plus the respective radiolabeled tracer. After incubation, explants are lightly blotted, weighed, and macromolecules precipitated with trichloroacetic acid. Soluble radiolabel, representing free amino acid taken up by the tissue, is counted and uptake is calculated. It is expected that mammary glands of sows overexpressing IGF-I will demonstrate increased nutrient uptake as compared to controls non-transgenic sows.

EXAMPLE 6

Effect of IGF-I on Piglet Intestinal Development

Piglets are sacrificed and intestinal samples prepared as described in Example 4B above. Samples are analyzed for morphology, digestive, and absorptive functions as described below.

A. GI Structure and Morphology

DNA and protein content of intestinal samples is determined using previously described methods (Houle et al., Pediatr. Res., 42:78 [1997]). Intestinal histomorpholgy is analyzed by embedding formulin-fixed iejunal samples in paraffin, slicing the samples to 5 μM with a microtome, and staining with hematoxylin. Villus height, villus width, crypt depth, and muscularis thickness are measured using a Nikon microscope (Fryer) and Image 1 software (Universal Imaging) in 10 vertically well-oriented villi and crypts. Crypt to villus ratios and villus cross-sectional area will be calculated (Houle et al., Pediatr. Res., 42:78 [1997]). It is expected that mirovillus height will be increased in piglets suckling transgenic sows as compared to piglets suckling non-transgenic control sows.

B. Disaccharidase Gene Expression

Lactase and sucrase steady state mRNA abundance is measured using standard methods. Total cellular RNA is isolated by the method of Chomczynski (Bio Techniques, 15:532 [1993]), size fractionated by agarose-gel electrophoresis and capillary transferred to nylon membranes (Houle et al., Pediatr. Res., 42:78 [1997]). Blots are hybridized with $^{32}$P-dCTP-labeled cDNA probes for lactase (Troelsen et al., J. Biol. Chem., 267:20407 [1992]), sucrase (Chandrasena et al., Cell. Mol. Biol., 38:243 [1992]). RNA expression is quantified using a phosphoimager (Molecular Dynamics) and lactase and sucrase expression is normalized to EF-1α expression. It is expected that disaccharidase acitivity will be increased in piglets suckling transgenic sows as compared to piglets suckling non-transgenic control sows.

C. Nutrient Transport and Ion Secretion

Jejunal and ileal samples are stripped of their muscularis, opened longitudinally, and mounted in an Ussing chamber apparatus (Physiologic Instruments). Mucosal and serosal surfaces (0.5 cm$^2$) are exposed to 10 mL oxygenated (95% $O_2$/5% $CO_2$) Krebs buffer pH 7.4 which is recirculated from a reservoir maintained at 37° C. After a 15 minute equilibration, spontaneous transmural potential difference (mV) and short circuit current are measured (Tappenden et al., 2000). Sodium-dependent nutrient transport is determined by marking the change in short circuit current induced by the addition of glucose and glutamine ($10^{-2}$ M) to the mucosal side of the Ussing chamber. Ion secretion is determined by quantifying the change in short-circuit current induced by the addition of chloride secretagogous ($10^{-4}$ serotonign and carbachol) to the media bathing the serosal side of the tissue. The Ussing chamber apparatus is connected to 4 dual channel voltage/current clamps (VCC MC2, Physiologic Instruments) which each have a computer interface allowing for real time data acquisition and subsequent analysis (Acquire and Analyze software, Physiologic Instruments). It is expected that Na$^+$ coupled glucose and glutamine transport will be increased in piglets suckling transgenic sows as compared to piglets suckling non-transgenic control sows.

D. Nutrient Transporter Gene Expression

Total cellular RNA is isolated and northern blots are prepared as described above (Example 6B). Blots are hybridized with cDNA probes for B$^0$ amino acid transporter, SGLT-1, and the Na$^+$, K$^+$-ATPase α1, and Na$^+$,K$^+$-ATPase β1 subunits. For GLUT2, blots are hybridized with an antisense riboprobe for GLUT2 generated from plasmid DNA (pGEM-4Z-HTL-3; obtained from G.I. Bell, University of Chicago) and T7 RNA polymerase (Tappenden et al., 1997). Membranes are probed for EF-1α and mRNA is quantified and normalized as described above (Example 6B). It is expected that Na$^+$, K$^+$-ATPase gene expression will be increased in piglets suckling transgenic sows as compared to piglets suckling non-transgenic control sows.

E. Nutrient Transporter Protein Abundance

The relative abundance of SGLT-1, GLUT2, and Na$^+$,K$^+$-ATPase proteins is identified in isolated brush border and basolateral membranes, respectively, by Western immunoblotting. Brush border and basolateral membranes are simultaneously isolated as described previously (Tappenden et al., 1998). Briefly, stripped mucosa are homogenized in 2.5 M sucrose-tris buffer and brush border and basolateral membrane fractions are separated by 3 sequential centrifugation steps. The brush border membrane fraction is further purified using a 20% Percoll gradient, followed by calcium chloride precipitation. The basolateral membrane fraction is further purified by calcium chloride precipitation. Membrane purity is confirmed through a 10 to 20 fold enrichment in activity of alkaline phosphatase (brush border) or Na$^+$, K$^+$-ATPase (basolateral) over the initial homogenate. Membrane proteins are separated by SDS-PAGE, electroblotted to nitrocellulose and immunoblotted using standard methods (Tappenden, et al., 1998). Polyclonal (rabbit anti-human) primary antibodies against GLUT2, SGLT-1 and Na$^+$, K$^+$-ATPase (Oncogene Science) are used. Bands are detected by chemiluminescence using the Supersignal CL-HRP Substrate System (Pierce) followed by exposure to Hyperfilm ECL (Amersham). Relative protein concentrations are determined by densitometry. It is expected that Na$^+$, K$^+$-ATPase, GLUT2, and SGLT-1 protein expression will be increased in piglets suckling transgenic sows as compared to piglets suckling non-transgenic control sows.

EXAMPLE 7

Generation of Alpha-Lactalbumin and IGF-I Transgenic Pigs

A new line of transgenic pigs was generated by mating alpha-lactalbumin transgenic sows to an IGF-I transgenic pig. Piglets were screened and gilts positive for both α-LA/IGF-I (n=7), α-LA alone (n=7), IGF-I alone (n=3) and negative for both transgenes (n=5) were bred to a York boar. Milk yield and piglet growth were assessed throughout lactation. Milk production of α-LA (6.56±0.042 kg) and α-LA/IGF-I transgenic (6.51±0.052 kg) were higher on day 7 of lactation than IGF-I (5.3±0.062 kg) or control (5.1±0.044 kg) sows. Body weight at weaning tended to be higher in the piglets suckling from sows positive for both transgenes, but the difference was not statistically significant at this point due to low sample size. The lines of transgenic swine created using mammary over-expression of α-LA, IGF-I or both provide means to improve pig production.

U.S. Pat. No. 5,850,000 (Bleck, et al., issued Dec. 15, 1998) and U.S. Pat. No. 5,530,177 (Bleck, et al., issued Jun. 25, 1996) are hereby incorporated by reference to the extent not inconsistent with the disclosure herewith.

All publications and patents mentioned in the above specification are herein incorporated by reference to the extent not inconsistent with the disclosure herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, developmental biology, biochemistry, or related fields are intended to be within the scope of the following claims.

What is claimed is:

1. A transgenic non-human mammal having a genome, said genome comprising a heterologous nucleic acid sequence encoding a growth factor and encoding alpha-lactalbumin operably linked to a mammary preferential promoter, wherein descendants of said transgenic mammal express an increased amount of growth factor in their milk and an increased amount of alpha-lactalbumin in their milk as compared to control non-transgenic mammals.

2. The transgenic non-human mammal of claim 1, wherein said growth factor is selected from the group consisting of insulin-like growth factor I, insulin-like growth factor II, epidermal growth factor, platelet-derived growth factor, fibroblast growth factor, and transforming growth factor.

3. The transgenic non-human mammal of claim 2, wherein said insulin-like growth factor I is selected from the group consisting of human, porcine, and bovine insulin-like growth factor I.

4. A transgenic non-human mammal having a genome, said genome comprising a heterologous nucleic acid sequence encoding an insulin-like growth factor I and encoding alpha-lactalbumin operably linked to a mammary preferential promoter, wherein descendants of said transgenic mammal express an increased amount of growth factor in their milk and an increased milk volume as compared to control non-transgenic mammals.

5. A method of increasing the volume of milk and the insulin-like growth factor I content of milk in transgenic nonhuman mammals, said method comprising: providing a transgenic non-human mammal having a genome, said genome comprising a heterologous nucleic acid sequence encoding an insulin-like growth factor I and encoding alpha-lactalbumin operably linked to a mammary preferential promoter, wherein said transgenic mammal expresses an increased amount of growth factor in its milk as compared to control non-human transgenic mammals.

6. A method of increasing the growth factor content of milk in non-human transgenic mammals, said method comprising: providing a non-human transgenic mammal having a genome, said genome comprising a heterologous nucleic acid sequence encoding a growth factor gene and encoding alpha-lactalbumin operably linked to a mammary preferential promoter, wherein said transgenic mammal expresses an increased amount of growth factor in its milk as compared to control non-transgenic mammals.

* * * * *

SEQUENCE LISTING

<160> NUMBER OF SEQ ID NOS: 2

<210> SEQ ID NO 1
<211> LENGTH: 4532
<212> TYPE: DNA
<213> ORGANISM: Artificial Sequence
<220> FEATURE:
<223> OTHER INFORMATION: Description of Artificial Sequence: alpha-LA/IGF-I gene construct

<400> SEQUENCE: 1

```
gatcagtcct gggtggtcat tgaaaggact gatgctgaag ttgaagctcc aatactttgg      60
ccacctgatg cgaagaactg actcatgtga taagaccctg atactgggaa agattgaagg     120
caggaggaga agggatgaca gaggatggaa gagttggatg gaatcaccaa ctcgatggac     180
atgagtttga gcaagcttcc aggagttggt aatgggcagg gaagcctggc gtgctgcagt     240
ccatggggtt gcaaagagtt ggacactact gagtgactga actgaactga tagtgtaatc     300
catggtacag aatataggat aaaaagagg aagagtttgc cctgattctg aagagttgta     360
ggatataaaa gtttagaata cctttagttt ggaagtctta aattatttac ttaggatggg     420
tacccactgc aatataagaa tcaggcttt agagactgat gtagagagaa tgagccctgg     480
cataccagaa gctaacagct attggttata gctgttataa ccaatatata accaatatat     540
tggttatata gcatgaagct tgatgccagc aatttgaagg aaccatttag aactagtatc     600
ctaaactcta catgttccag gacactgatc ttaaagctca ggttcagaat cttgtttat     660
aggctctagg tgtatattgt ggggcttccc tggtggctca gatggtaaag tgtctgcctg     720
caatgtgggt gatctgggtt cgatccctgg cttgggaaga tcccctggag aaggaaatgg     780
caacccactc tagtactctt acctggaaaa ttccatggac agaggagcct tgtaagctac     840
agtccatggg attgcaaaga gttgaacaca actgagcaac taagcacagc acagtacagt     900
atacacctgt gaggtgaagt gaagtgaagg ttcaatgcag ggtctcctgc attgcagaaa     960
gattctttac catctgagcc accagggaag cccaagaata ctggagtggg tagcctattc    1020
cttctccagg ggatcttccc atcccaggaa ttgaactgga gtctcctgca tttcaggtgg    1080
attcttcacc agctgaacta ccaggtggat actactccaa tattaaagtg cttaaagtcc    1140
agttttccca ccttccccaa aaaggttggg tcactctttt ttaaccttct gtggcctact    1200
ctgaggctgt ctacaagctt atatatttat gaacacattt attgcaagtt gttagtttta    1260
gatttacaat gtggtatctg ctatttagt ggtattggtg gttggggatg gggaggctga    1320
tagcatctca gagggcagct agatactgtc atacacactt tcaagttct ccattttgt     1380
gaaatagaaa gtctctggat ctaagttata tgtgattctc agtctctgtg gtcatattct    1440
attctactcc tgaccactca acaaggaacc aagatatcaa gggacacttg ttttgtttca    1500
tgcctgggtt gagtgggcca tgacatatga tgatgtacag tccttttcca tattctgtat    1560
gtctctaaga ggaaggagga gttggccgtg gacccctttgt gcattttctg attgcttcac    1620
ttgtattacc cctgaggccc cctttgttcc tgaaataggt tgggcacatc ttgcttccta    1680
gaaccaacac taccagaaac aacataaata aagccaaatg gaaacaggta tcatgttttgt   1740
aacactcttt gggcaggtaa caataccctag tatggactag agattctggg gaggaaagga    1800
aaagtggggt gaaattactg aaggaagctc aatgtttctt tgttggtttt actggcctct    1860
cttgtcatcc tcttcctgga tgtaaggctt gatgccaggg cccctaaggc tttttccaca    1920
```

```
aataaaagga ggtgagcagt gtggtgaccc catttcagaa tcttgagggg taacgaattc    1980
taaccaaaat gatgtccttt gtctctctgc tcctggtagg aatcctattc catgccaccc    2040
aggctggacc ggagacgctc tgcgggggctg agctggtgga tgctcttcag ttcgtgtgtg   2100
gagacagggg attttatttc aacaagccca caggtatgg atccagcagt cggagggcgc    2160
cccagacagg catcgtggat gagtgctgct tccggagctg tgatctaagg aggctggaga    2220
tgtattgcgc accCctaaag cctgccaagt cagcttgata gctcgacgga tccccaaaat    2280
gtgaggtgtt ccgggagctg aaagacttga agggctacgg aggtgtcagt ttgcctgaat    2340
gtgagttccc tgctattttg ctttgtccca taattcatcc tcttcactct ttccctccat    2400
tctcttcatc ctcttttccc cctctacttt taattatcaa acaattctct tatttgttta    2460
ctcttttatt acatttattt atctgcctct cctttttccc attgtctgat cctttggaac    2520
tcttttcacc ttaacaagat actctgtggt ctgccatatt tggagattgg ttggagagcc    2580
tttttcggtc tgggaataca ggtcctcatt tatgctatac atgaacatcc ttgtgaaatc    2640 tcttttcgt ctttctttca ggggtctgta ccgcgtttca taccagtggt tatgacacac     2700
aagccatagt acaaaacaat gacagcacag aatatggact cttccagata aataataaaa    2760
tttggtgcaa agacgaccag aaccctcact caagcaacat ctgtaacatc tcctgtgaca    2820
gtgagtaact tcttttact ctgttcctgt gtttttctga aacctactcc tgggataacc     2880
tccttttttt tggtgtgaag cacacctctg gcttcactgc cttggactcc aaattaactg    2940
tgggacttga taataccgag taagaggctc ttagaatttt tcattaacac taaatcccca    3000
gacagtttct taaagttcct gggtaggtga cctgagctgt ttggggatct tgatgtataa    3060
tacCctgtat tttcagacta agttggttga tgaagttgat aattcctaag gagctgcccc    3120
agagaagaga agggagtcct tacctaggga taggcattac tgtattaaat ttctcaccca    3180
gaaggcaaca ggcataagcc tctagttcag agaaaaccag agaagaggga aattcattat    3240
ccttctgggt aatacttagc tctctcattt tttccaccag aggctcctgc cagagttcct    3300
ggatgatgat cttactgatg acattatgtg tgtcaagaag attctggata agtaggaat    3360 taactactgg tgagtcacct ctctattttt cacttaatct ttcctctctt tcttctcagt    3420
cctttcgtcc cagcactata ctccttctctc tctatttctt ggtcttttaa gctagaatgt    3480
aatcttaaaa acaaaaatca tcaagcagac tccggtttcc aattttgaag cttcacttac    3540
ttcactcccg ttagcaattt tcctacctaa gggtccctaa tagagggctg agatccagga    3600
tttccttcac caggacttga acatctaatt ctacttgttc agtcctacat cctaaggcac    3660 gcccttgac cactgccccg caattttctt ggagttttaa aaaatggacc ttactccact     3720
aagtggctca gtgtctctag ccatgtggct aggaaagtct gtctgtaatt ttaacccaca    3780
gtcttccacc tcagccttcc tggggataaa gctagatgta aatctaacca agatcctgtc    3840
agtaatttgc cttgtctcct tcttcatgat caggttggcc cataaagcac tctgttctga    3900
gaagctggat cagtggctct gtgagaagtt gtgaacacct gctgtctttg ctgcttctgt    3960
cctctttctg ttcctggaac tcctctgccc cgtggctacc tcgttttgct tctttgtacc    4020
cccttgaagc taactcgtct ctgagccctg ggccctgtag tgacaatgga catgtaagga    4080
ctaatctcca ggtgtgcatg aatggcgctc tggacttttg acccttgctc gatgtccctg    4140
atggcgcttt taatgcaaca gtacatattc cacttttgtc ccgaataaaa agcctgattt    4200
tgagtggctg gctgtatttt cttcctggtg ggagagggag gaaatagggt gagtaggtag    4260
acctggccat gggtcacaga ccccttcatc tctactaaag aggatagaga ggctgaactt    4320
```

```
                                                    -continued
ataacaactc aaagatggag attactttct gtattaattc aattcaacag agttttattg    4380
atcacctagc ataatttaaa gagctatgga ggggatctaa agttgactaa aagcatctct    4440
tacctaaact gctgctaagt cacttcagtt gtgtccgact ctgtgtgacc ccatagacgg    4500
tagcccacaa ggctcccatg tccctggaat tc                                  4532

<210> SEQ ID NO 2
<211> LENGTH: 210
<212> TYPE: DNA
<213> ORGANISM: Artificial Sequence
<220> FEATURE:
<223> OTHER INFORMATION: Description of Artificial Sequence:IGF-I

<400> SEQUENCE: 2
ggaccggaga cgctctgcgg ggctgagctg gtggatgctc ttcagttcgt gtgtggagac      60
aggggatttt atttcaacaa gcccacaggg tatggatcca gcagtcggag ggcgccccag     120
acaggcatcg tggatgagtg ctgcttccgg agctgtgatc taaggaggct ggagatgtat     180
tgcgcacccc taaagcctgc caagtcagct                                       210
```